United States Patent
Karin

(12) 
(10) Patent No.: US 6,420,346 B1
(45) Date of Patent: Jul. 16, 2002

(54) POLYNUCLEOTIDES ENCODING MIP-1α, MCP-1, MIP-1β, RANTES AND TNF-α, AND METHODS FOR TREATING RHEUMATOID ARTHRITIS

(75) Inventor: Nathan Karin, Haifa (IL)

(73) Assignee: Rappaport Family Institute for Research in the Medical Sciences, Haifa (IL)

( * ) Notice: Subject to any disclaimer, the term of this patent is extended or adjusted under 35 U.S.C. 154(b) by 0 days.

(21) Appl. No.: 09/498,625

(22) Filed: Feb. 7, 2000

(51) Int. Cl.[7] .................. A61K 38/00; C12N 15/36
(52) U.S. Cl. .............................. 514/44; 435/455
(58) Field of Search .................. 514/44; 424/93.21, 424/93.2; 536/23.1; 435/455

(56) References Cited

PUBLICATIONS

Kasama et al., Journal of Clinical Investigation 95:2868–2876, Jul. 1995.*
Feldmann et al. Annual Review in Immunology 14:397–440, 1996.*
Brennan et al. Cytokines in autoimmunity 8(6):872–877, Dec. 1996.*
Cao et al. Gastroenterology 112(2):501–510, 1997.*
Karin et al. IMAJ 2(Suppl)63–68, Jul. 2000.*
Youssef et al. The Journal of Immunology 161(8):3870–3879, Oct. 1998.*

* cited by examiner

*Primary Examiner*—Deborah Crouch
*Assistant Examiner*—Joseph T. Woitach
(74) *Attorney, Agent, or Firm*—G. E. Ehrlich Ltd.

(57) ABSTRACT

A method of treating rheumatoid arthritis of an individual is disclosed. The method comprises the step of expressing within the individual at least an immunologically recognizable portion of a cytokine from an exogenous polynucleotide encoding the at least a portion of the cytokine, wherein a level of expression of the at least a portion of the cytokine is sufficient to induce the formation of anti-cytokine immunoglobulins which serve for neutralizing or ameliorating the activity of a respective and/or cross reactive endogenous cytokine, to thereby treat rheumatoid arthritis.

1 Claim, 20 Drawing Sheets

(6 of 20 Drawing Sheet(s) Filed in Color)

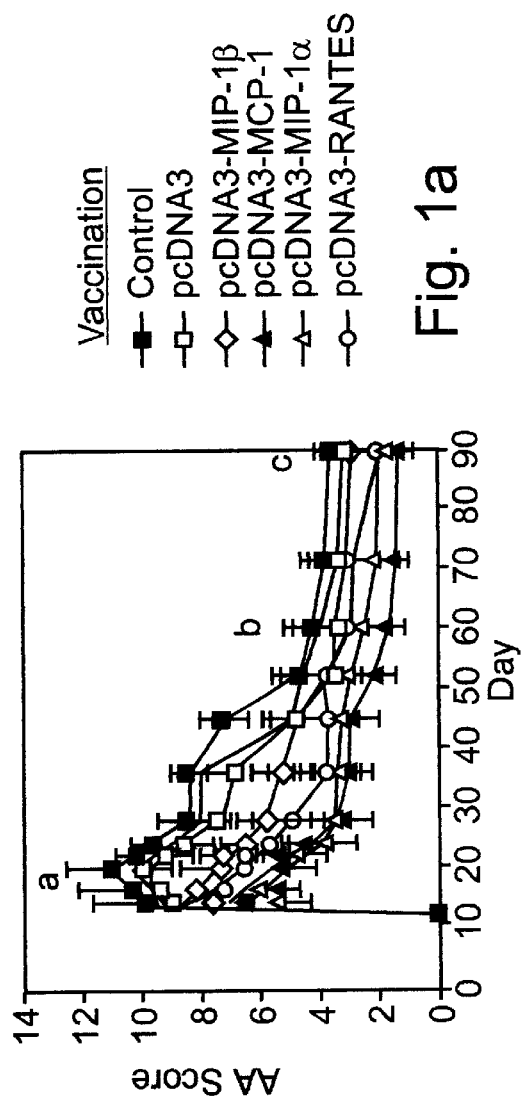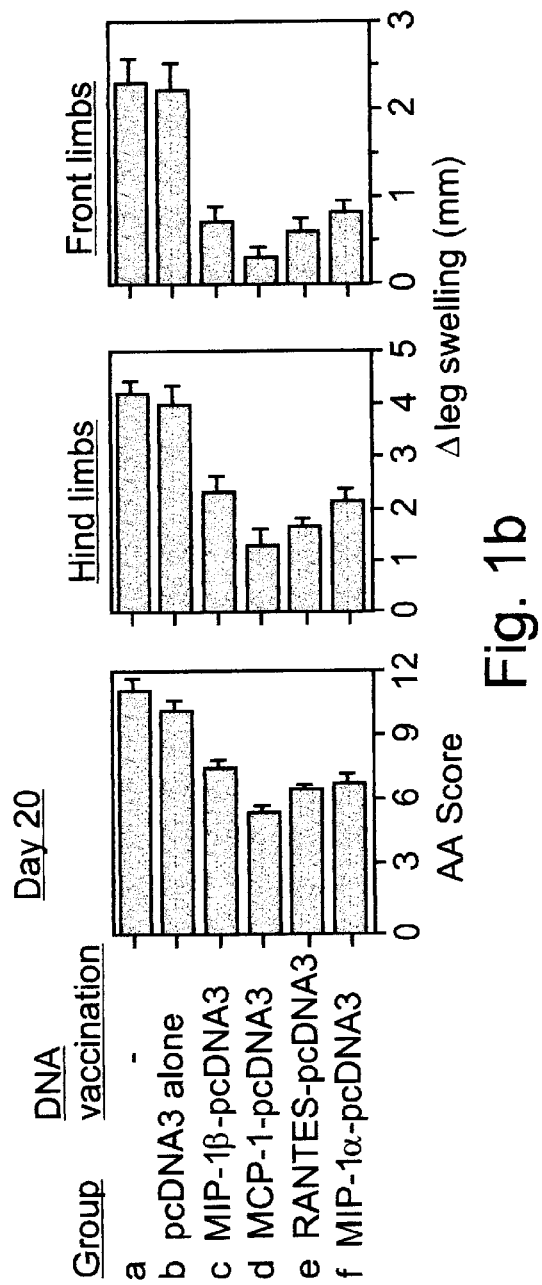

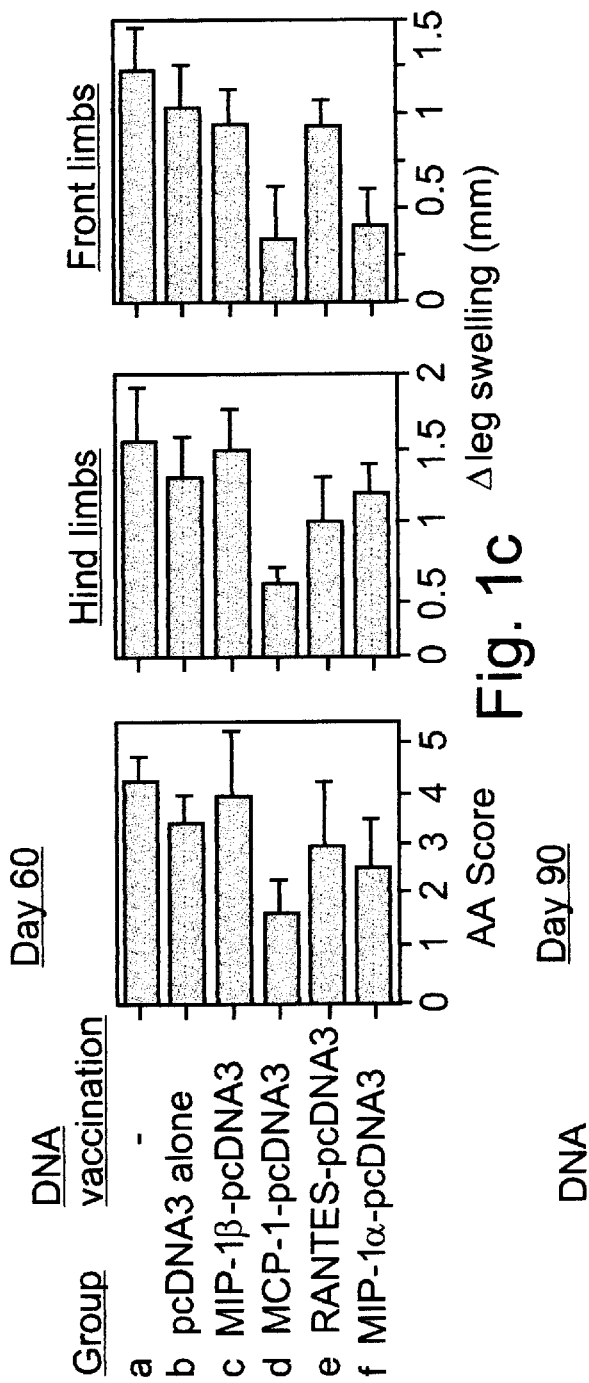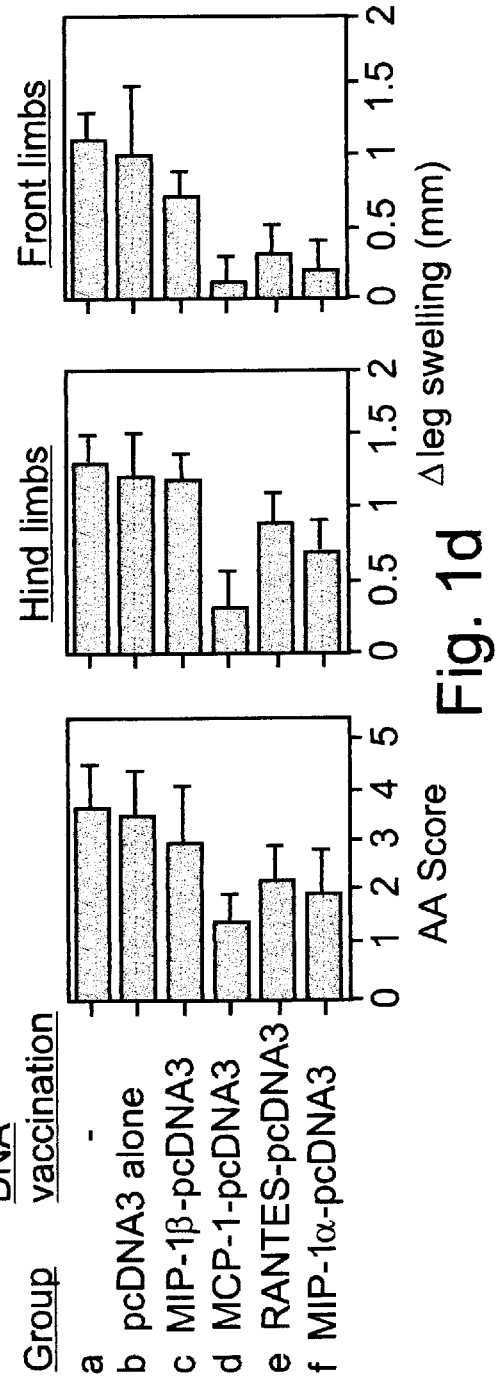

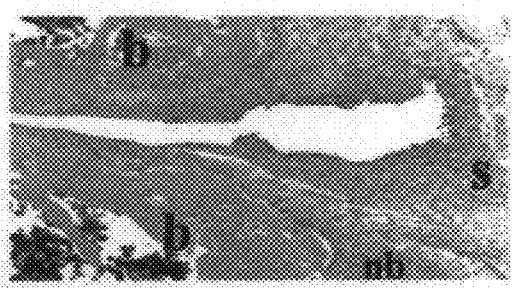
Fig. 2a     Fig. 2b
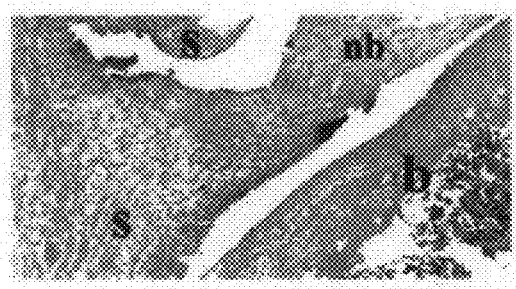
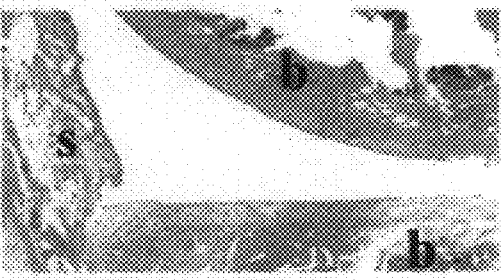
Fig. 2c     Fig. 2d
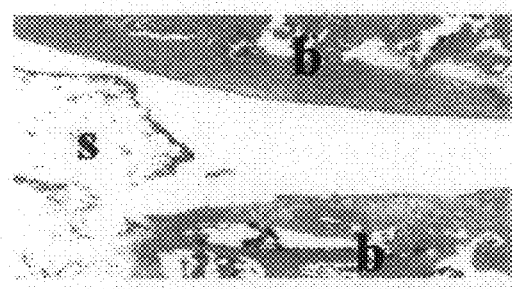
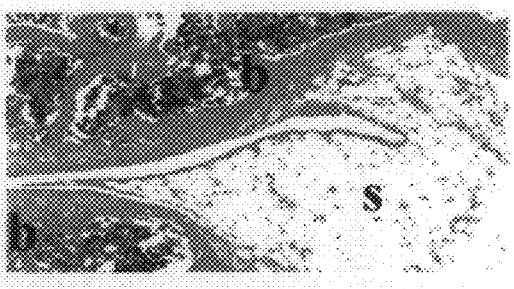
Fig. 2e     Fig. 2f
Fig. 2g

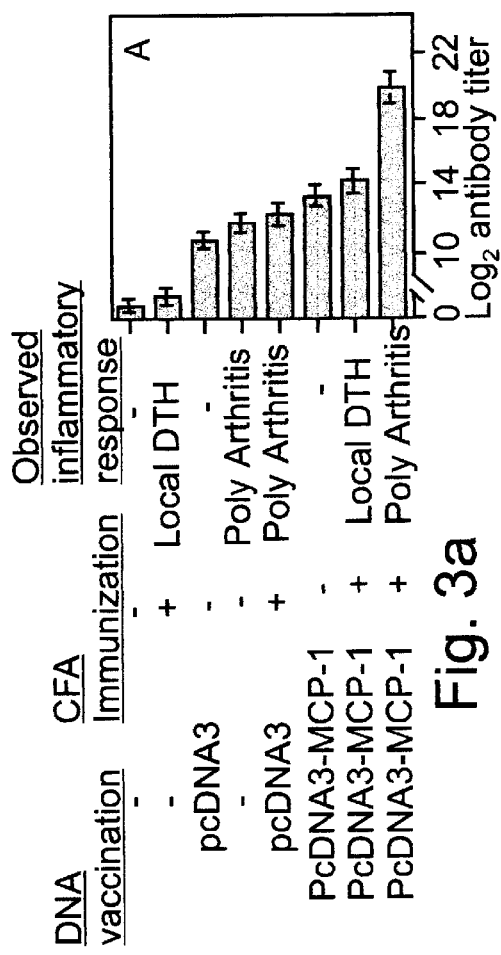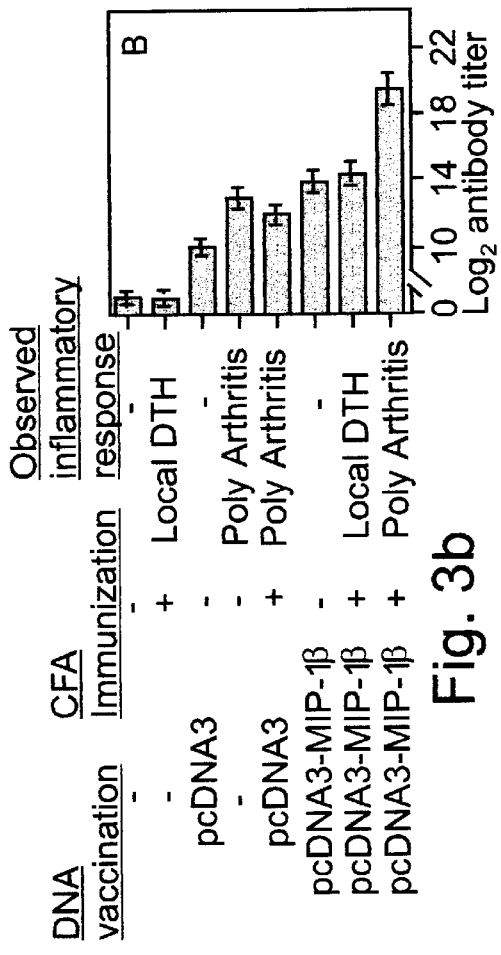
Fig. 3a
Fig. 3b

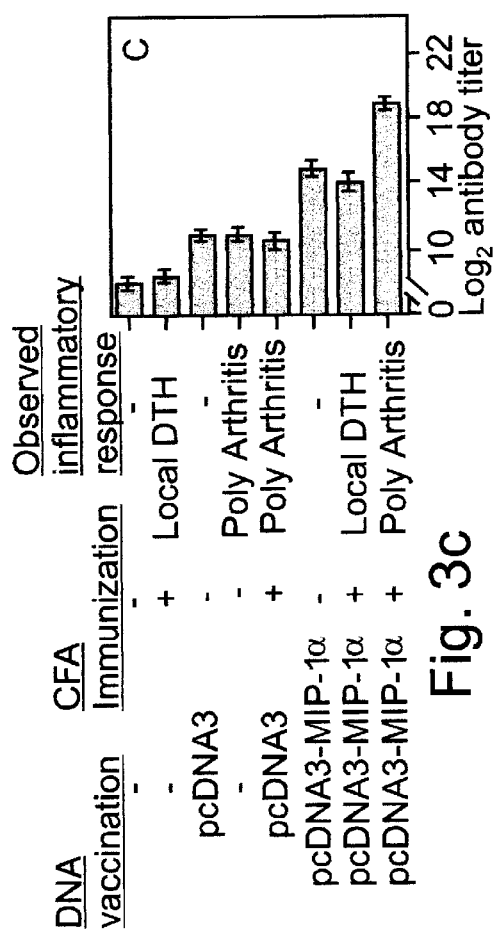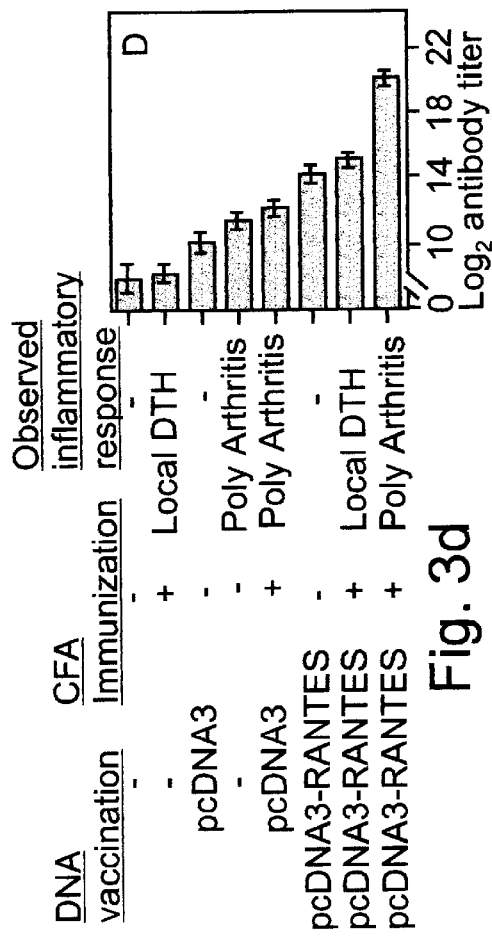
Fig. 3c
Fig. 3d

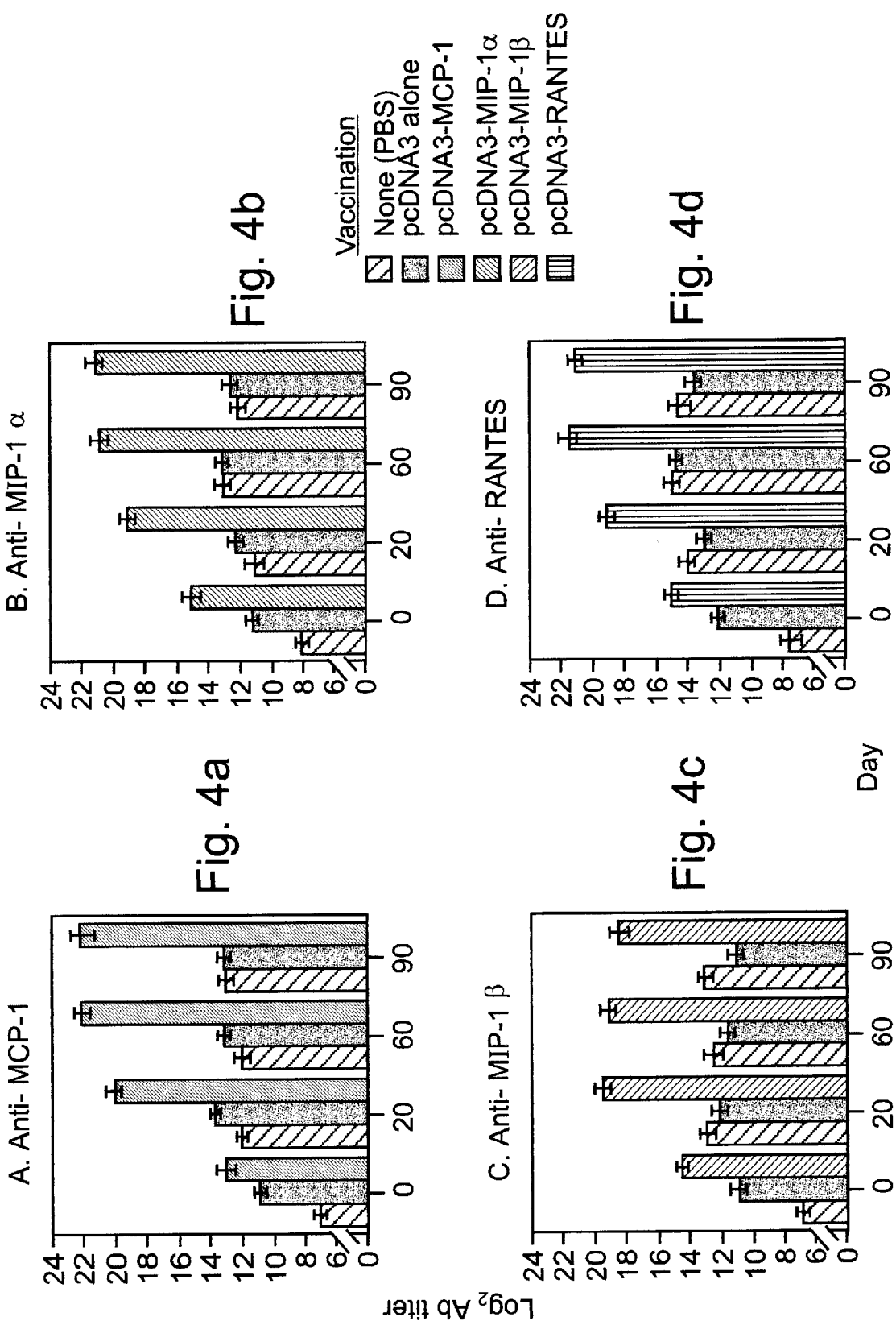

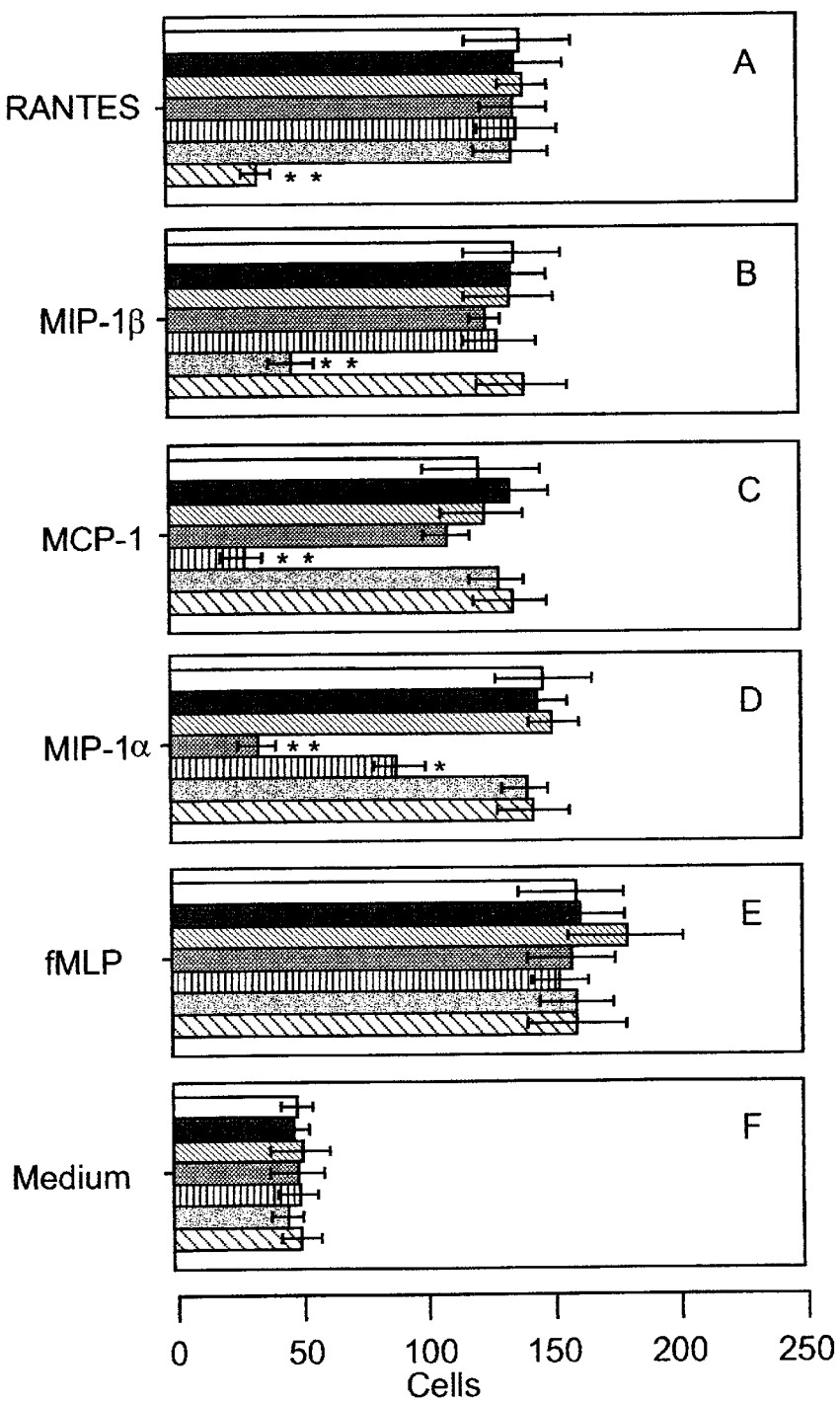

Day

Replacement therapy

◇ Only PBS
■ IgG from naive rats
○ IgG from AA rats
□ IgG from AA rats immunized with pcDNA3
△ IgG from AA rats immunized with pcDNA3-MIP-1α
▲ IgG from AA rats immunized with pcDNA3-MCP-1
◆ IgG from AA rats immunized with pcDNA3-MIP-1β
▽ IgG from AA rats immunized with pcDNA3-RANTES

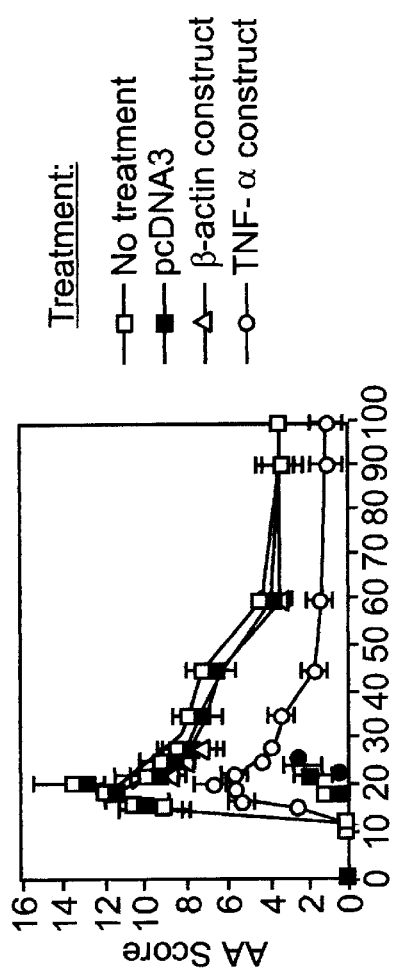
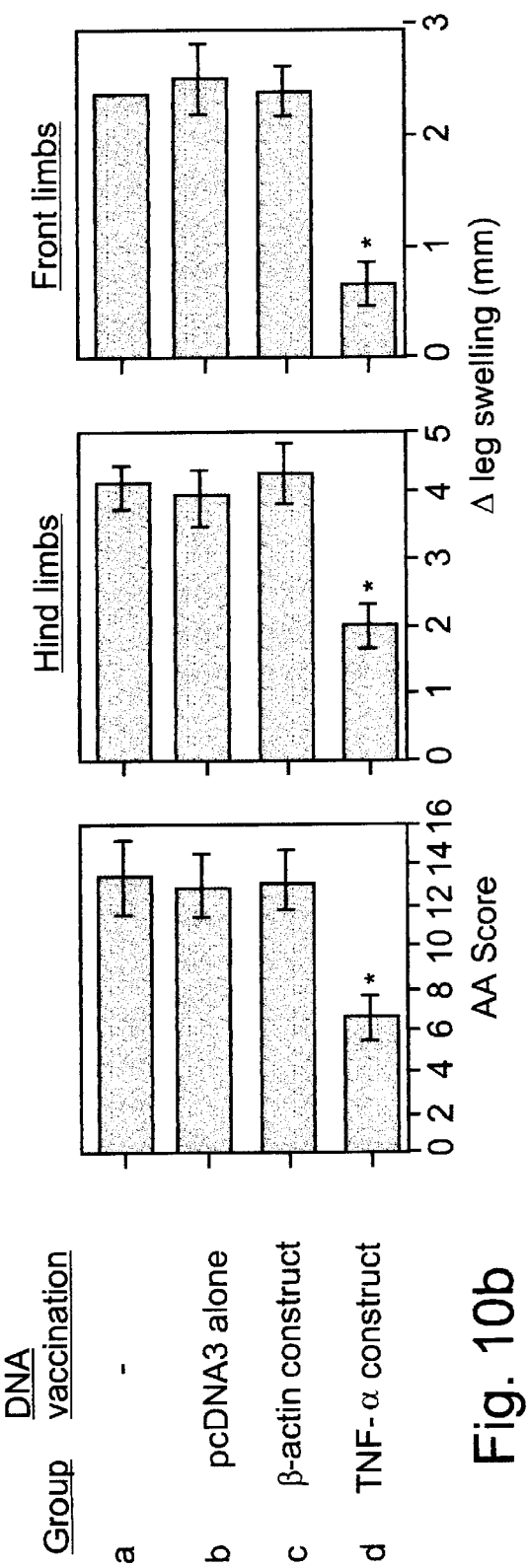
Fig. 10a
Fig. 10b

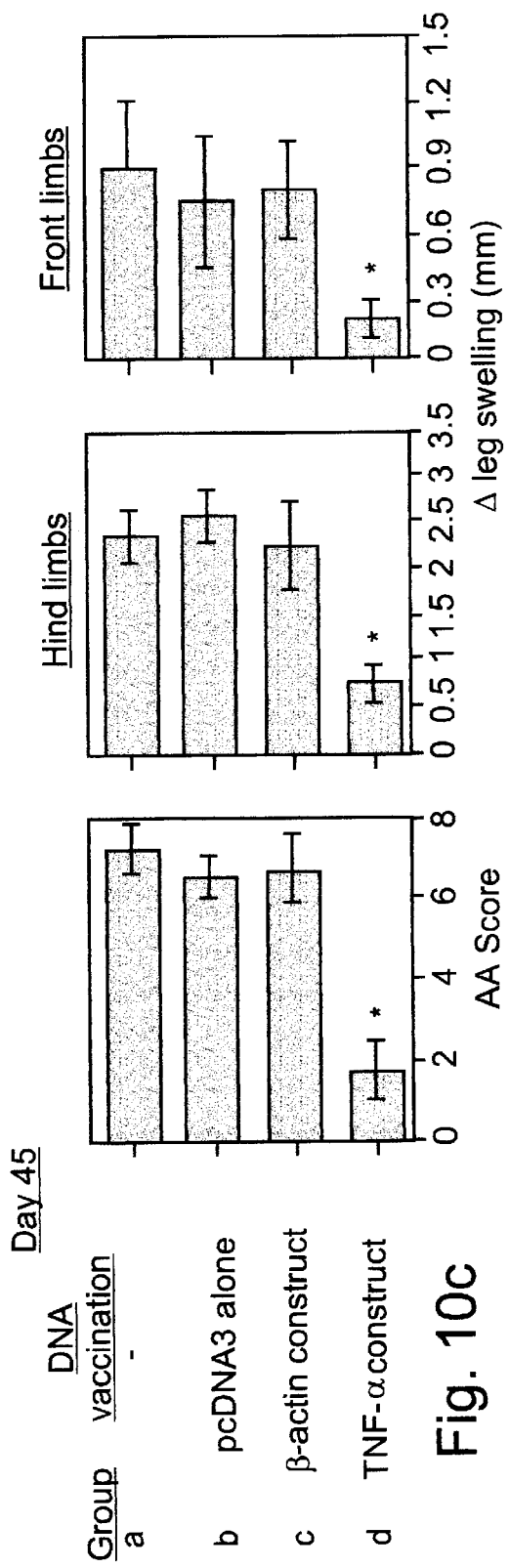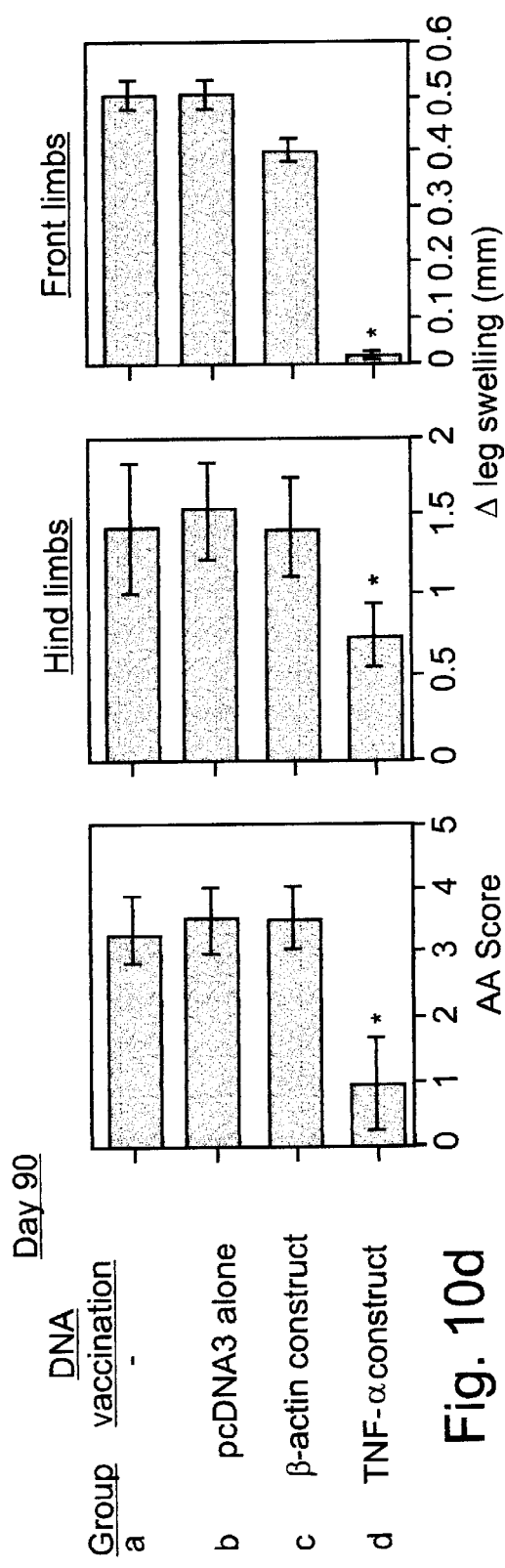

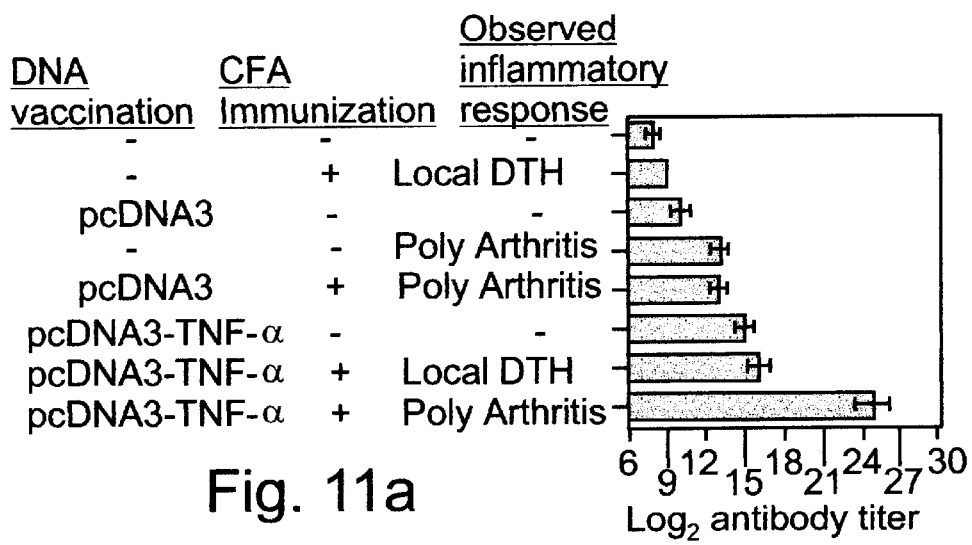
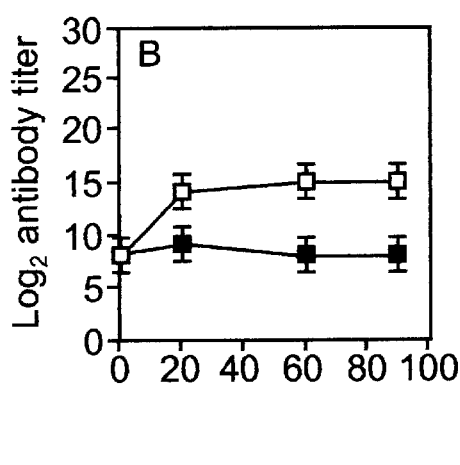 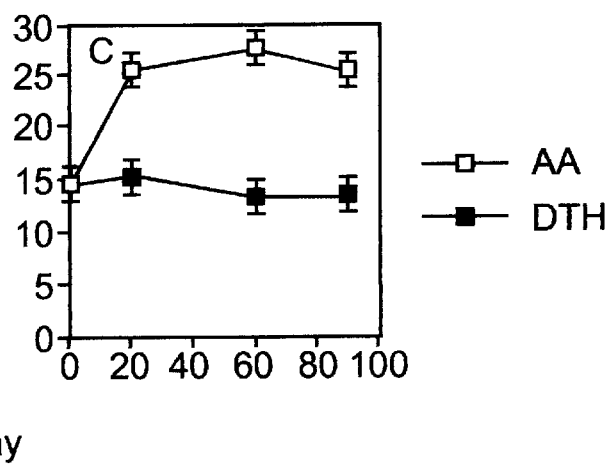
Fig. 11a
Fig. 11b    Fig. 11c

POLYNUCLEOTIDES ENCODING MIP-1α, MCP-1, MIP-1β, RANTES AND TNF-α, AND METHODS FOR TREATING RHEUMATOID ARTHRITIS

FIELD AND BACKGROUND OF THE INVENTION

The present invention relates to pharmaceutical compositions and methods for treating rheumatoid arthritis in an individual. More particularly, the present invention relates to DNA vaccination approaches which induce the breakdown of self-tolerance to cytokines and as such inhibit the progression of the disease.

Rheumatoid arthritis (RA) is an inflammatory disorder characterized by infiltration of leukocytes into the synovial tissue (ST) and synovial fluid (SF) of joints (Harris, 1990). Depending on the type of immunization, a single administration of complete Freund's adjuvant (CFA) may result in the development of a local inflammatory process or chronic poly adjuvant induced arthritis (AIA, also termed AA) which histologically and clinically resembles human RA (Holoshitz et al., 1983). In the scientific and medical communities, AIA is considered a reliable animal model for testing drugs and treatments for RA.

In both diseases proinflammatory cytokines and chemokines are believed to play a pivotal role in the attraction of leukocytes to the site of inflammation and in the initiation and progression of the inflammatory process. The role of proinflammatory cytokines, particularly TNF-α and IL-1, in disease manifestation has been intensively studied and explored in experimental models that have been expanded to clinical trials (Arend and Dayer, 1995; Arend et al., 1994; Elliott et al., 1994; Feldmann et al., 1997; Moreland et al., 1997; Moreland et al., 1996; for a general review, see also, Feldmann et al., 1996). Other cytokines such as IL-4, TGF-β, IL-8, IL-17, IL-10, IL-11, IL-12 and IL-15 have also been implicated in the regulation of the disease. Such regulation can be attributed to either their direct effect on disease manifestation, their synergistic effect with other proinflammatory cytokines/chemokines, or their involvement in the regulation of chemokine transcription, and production (Badolato and Oppenheim, 1996; Badolato et al., 1997; Butler et al., 1999; Chabaud et al., 1998; Evans et al., 1998; Feldmann et al., 1996; Kasama et al., 1999; Ma et al., 1998; Parks et al., 1998; Sato et al., 1996; Schimmer et al., 1998; Schrier et al., 1998; Wahl et al., 1993).

Chemokines are chemoattractant cytokines that mediate leukocyte attraction and recruitment at the site of inflammation. Based on the positions of the first two cysteines, chemokines can be divided into four highly conserved but distinct supergene families, C—C, C-X-C, C and C-X3-C (Rollins, 1997; Sallusto et al., 1998; Ward et al., 1998). The C—C family is primarily involved in the activation of endothelium and chemoattraction of T cells and monocytes to the site of inflammation. The protective competence of anti-C—C chemokine based immunotherapy has been demonstrated in experimental autoimmune encephalomyelitis (EAE), and AA.

Neutralizing the activity of chemokines as a way to treat arthritis has been explored by several researchers. In a very recent study neutralizing antibodies to epithelial neutrophil activating peptide 78 (ENA-78) were found capable of inhibiting the development of AA if administered before but not after the onset of disease (Halloran et al., 1999). In another recent study Barnes et al. used anti-human RANTES to ameliorate AA in the Lewis rat (Barnes et al., 1998). Gong et al. used an antagonist of Monocyte Chemoattractant Protein 1 (MCP-1) to inhibit arthritis in the MRL-1pr mouse model (Gong et al., 1997). Using a streptococcal cell wall induced arthritis model it has been shown that anti-IL-4 and anti MCP-1 antibodies block the disease (Schimmer et al., 1998). The same study demonstrated that neutralizing IL-4 by itself, leads to a marked reduction in MCP-1 mRNA transcription at the autoimmune site and to inhibition of the development of disease which further implicates MCP-1 in playing an active role in arthritis development.

A major disadvantage in treating chronic diseases with xenogenic neutralizing antibodies lies in their immunogenicity. This has motivated investigators to develop chimeric humanized antibodies, and monoclonal antibodies engineered with human Ig heavy and light chain from yeast artificial chromosomes (YAC) (Green et al., 1994). However, following repeated immunization, these engineered antibodies do trigger an apparent allotypic response.

The present invention provides an alternative therapeutic approach to the treatment of rheumatoid arthritis. This approach utilizes ex-vivo or in-vivo DNA vaccination with either cell contained DNA or preferably naked DNA constructs which include an expressible cytokine, preferably chemokine, derived coding sequence(s). The approach of the present invention enables overexpression of the cytokine in the recipient subject, thereby eliciting an immune response which induces the breakdown of self-tolerance to these cytokine and as such inhibit the progression of the disease.

As is further described in the examples section below, this therapeutic approach is of great advantage over prior art methods since it results in the generation of immunity to autologous antigens, which immunity level corresponds with a disease state. This type of therapy is ideally suited for treating rheumatoid arthritis.

SUMMARY OF THE INVENTION

According to one aspect of the present invention there is provided a method of treating rheumatoid arthritis of an individual, the method comprising the step of expressing within the individual at least an immunologically recognizable portion of a cytokine from an exogenous polynucleotide encoding the at least a portion of the cytokine, wherein a level of expression of the at least a portion of the cytokine is sufficient to induce a formation of anti-cytokine immunoglobulins, the anti-cytokine immunoglobulins being for neutralizing or ameliorating an activity of a respective and/or cross reactive endogenous cytokine, to thereby treat rheumatoid arthritis.

According to another aspect of the present invention there is provided a pharmaceutical composition comprising, as an active ingredient, a nucleic acid construct including a polynucleotide region encoding at least a portion of a cytokine and a pharmaceutically acceptable carrier.

According to further features in preferred embodiments of the invention described below, the cytokine is a chemokine.

According to still further features in the described preferred embodiments the chemokine is a C—C chemokine.

According to still further features in the described preferred embodiments the C—C chemokine is selected from the group consisting of MIP-1α, MCP-1, MIP-1β and RANTES.

According to still further features in the described preferred embodiments the cytokine is TNF-α.

According to still further features in the described preferred embodiments the step of expressing within the individual the at least an immunologically recognizable portion of the cytokine from the exogenous polynucleotide encoding the at least a portion of the cytokine is effected by administering the exogenous polynucleotide to the individual.

According to still further features in the described preferred embodiments the exogenous polynucleotide forms a part of a pharmaceutical composition.

According to still further features in the described preferred embodiments the pharmaceutical composition also includes a pharmaceutically acceptable carrier.

According to still further features in the described preferred embodiments the pharmaceutically acceptable carrier is selected from the group consisting of a viral carrier, a liposome carrier, a micelle carrier and a cellular carrier.

According to yet another aspect of the present invention there is provided a method of treating rheumatoid arthritis in an individual, the method comprising the step of administering to the individual cells expressing from an exogenous polynucleotide at least an immunologically recognizable portion of a cytokine, wherein a level of expression of the at least a portion of the cytokine is sufficient to induce a formation of anti-cytokine immunoglobulins, the anti-cytokine immunoglobulins being for neutralizing or ameliorating an activity of a respective and/or cross reactive endogenous cytokine, to thereby treat rheumatoid arthritis.

According to still another aspect of the present invention there is provided a cellular vaccine composition comprising cells expressing at least one peptide epitope derived from a cytokine, the at least one peptide includes at least 6 amino acid residues.

According to still further features in the described preferred embodiments the cells are selected from the group consisting of dendritic cells, macrophages, B cells and fibroblasts.

According to still further features in the described preferred embodiments the cells are derived from the individual.

According to still further features in the described preferred embodiments the cells secrete the at least a portion of the cytokine following expression thereof.

According to still further features in the described preferred embodiments the cells are antigen presenting cells and as such, the cells present portions of the cytokine following expression of the at least a portion of the cytokine.

According to an additional aspect of the present invention there is provided a method of treating rheumatoid arthritis of an individual, the method comprising the step of expressing within the individual an exogenous polynucleotide encoding at least a portion of a variable region of an anti-cytokine immunoglobulin, wherein a level of expression of the at least a portion of the variable region of the anti-cytokine immunoglobulin is sufficient for neutralizing or ameliorating an activity of a respective and/or cross reactive endogenous cytokine, to thereby treat rheumatoid arthritis.

According to yet an additional aspect of the present invention there is provided a pharmaceutical composition comprising, as an active ingredient, a nucleic acid construct including a polynucleotide region encoding at least a portion of a variable region of an anti-cytokine immunoglobulin and a pharmaceutically acceptable carrier, wherein the at least a portion of the variable region is capable of binding the cytokine.

According to still further features in the described preferred embodiments the variable region is a light chain variable region of the anti-cytokine immunoglobulin.

According to still further features in the described preferred embodiments the variable region is a heavy chain variable region of the anti-cytokine immunoglobulin.

According to still further features in the described preferred embodiments the cytokine is a chemokine.

According to still further features in the described preferred embodiments the chemokine is a C—C chemokine.

According to still further features in the described preferred embodiments the C—C chemokine is selected from the group consisting of MIP-1α, MCP-1, MIP-1β and RANTES.

According to still further features in the described preferred embodiments the cytokine is TNF-α.

According to still an additional aspect of the present invention there is provided a method of treating rheumatoid arthritis of an individual, the method comprising the step of administering to the individual cells expressing an exogenous polynucleotide encoding at least a portion of a variable region of an anti-cytokine immunoglobulin, wherein a level of expression of the at least a portion of the variable region of the anti-cytokine immunoglobulin is sufficient for neutralizing or ameliorating an activity of a respective and/or cross reactive endogenous cytokine, to thereby treat rheumatoid arthritis.

According to a further aspect of the present invention there is provided a cellular vaccine composition comprising cells expressing at least a portion of a variable region of an anti-cytokine immunoglobulin, wherein the portion of the variable region of the anti-cytokine immunoglobulin is capable of binding the cytokine.

According to still further features in the described preferred embodiments the cells secrete the at least a portion of the variable region of the anti-cytokine immunoglobulin following expression thereof.

The present invention successfully addresses the shortcomings of the presently known configurations by providing pharmaceutical compositions and methods useful in treating an individual suffering from rheumatoid arthritis

BRIEF DESCRIPTION OF THE DRAWINGS

The file of this patent contains at least one drawings executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show more detail than is necessary for a fundamental understanding of the invention, the description taken with the drawings making apparent to those skilled in the art how the several forms of the invention may be embodied in practice.

In the drawings:

FIGS. 1a–d depict leg swelling and clinical scores (as described in the Examples section) of control unimmunized rats, rats immunized with control DNA (pcDNA3) and rats immunized with various chemokine expression constructs. Clinical score and the differences in leg swelling are show as mean of 10 rats (days 10–30), or 6 rats (day 31-on) ±standard error (SE).

Figure 2H:
Figure 2I:
Figure 2J:
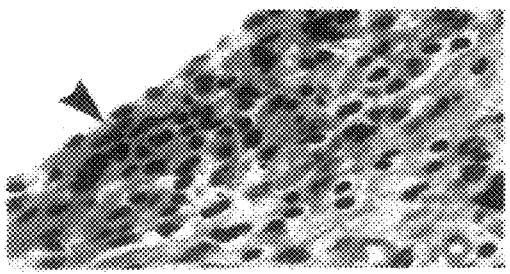
Figure 2K:
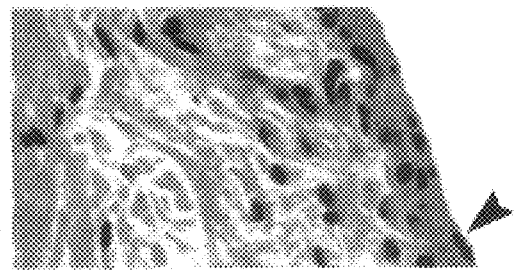
Figure 2L:
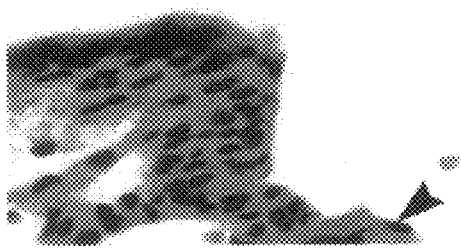
Figure 2M:
Figure 2N:

FIGS. 2a–n depict histological sections from control and chemokine immunized rats presented in Table 1 of Example 1. FIGS. 2a–g are magnified 5 times while FIGS. 2h–n are magnified 40 times. FIGS. 2a and 2h are sections from a non-diseased rat joint; FIGS. 2b and 2i—arthritic joint; FIGS. 2c and 2j—joint sections from rat vaccinated with pcDNA3 vector alone; FIGS. 2d and 2k—joint sections from rats vaccinated with MCP-1; FIGS. 2e and 2l—joint sections from rats vaccinated with MIP-1α; FIGS. 2f and 2m—joint sections from rats vaccinated with MIP-1β; FIGS. 2g and 2n—joint sections from rats vaccinated with RANTES. The arrowheads point to the synovial lining (b=bone; nb=new bone formation; s=synovial membrane).

FIGS. 3a–d depict anti-self antibody titers in serum of Lewis rats which were subjected to vaccination with the various C—C chemokine DNA constructs described in Example 1. Control rats were injected with pcDNA3 alone or with PBS. Three weeks post immunization, these rats were separated to sub-groups that were administered with CFA either by a foot pad injection to induce a local DTH response or by a tail-base administration to induce poly-arthritis. Results are shown as mean of three different serum samples±SE.

FIGS. 4a–d depict kinetics of anti-self antibody appearance in serum of Lewis rats vaccinated with the various C—C chemokine DNA constructs described above. Control rats were injected with pcDNA3 alone or with PBS. Three weeks later these rats were administered with CFA to induce poly-arthritis.

FIGS. 5a–d depict possible antibody cross-reactivity between rats vaccinated with MCP-1, MIP-1α, MIP-1β and RANTES constructs. Results are shown as mean of three different sera samples ±SE.

FIGS. 6a–f depict the competence of self-specific antibodies obtained in DNA vaccinated AA rats (FIGS. 5a–d) for inhibiting the migration of oil-induced peritoneal macrophages in a Boyden chemotaxis chamber assay. fMLP ($10^{-7}$M, Sigma) was used as a positive control for chemoattraction. Commercially available (Chemicon) MIP-1α (200 ng/ml), MCP-1, MIP-1β and RANTES (100 ng/ml each) were used as chemoattractants. Purified antibodies (IgG purification) were added at a concentration of 10 μg/ml. Result are shown as mean of triplicates ±SE.

Figure 7A:
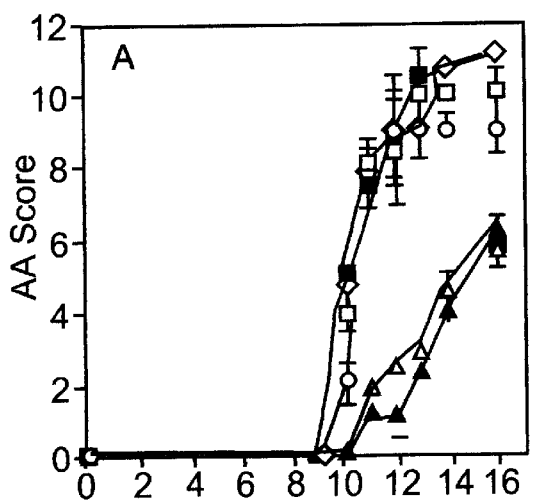
Figure 7B:
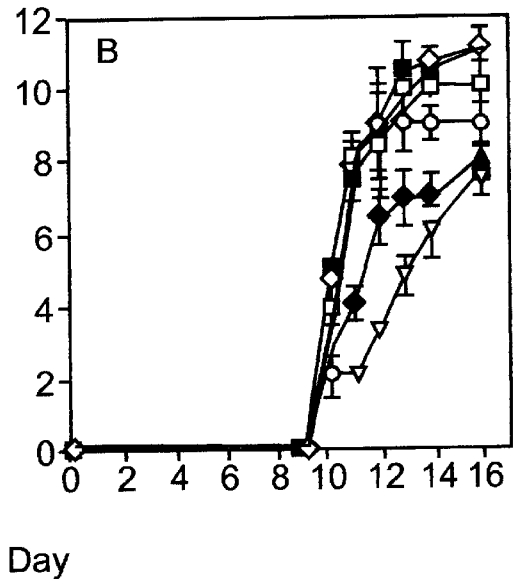

FIGS. 7a–b depict AA scoring of poly-arthritis diseased rats challenged Seven, ten and twelve days following the active induction of the disease with 200 μg of IgG (protein G purification, CNBr purification) derived from the different vaccination groups described in the Examples section. Results are shown as mean clinical score of six rats in each group ±SE.

Figure 8A:
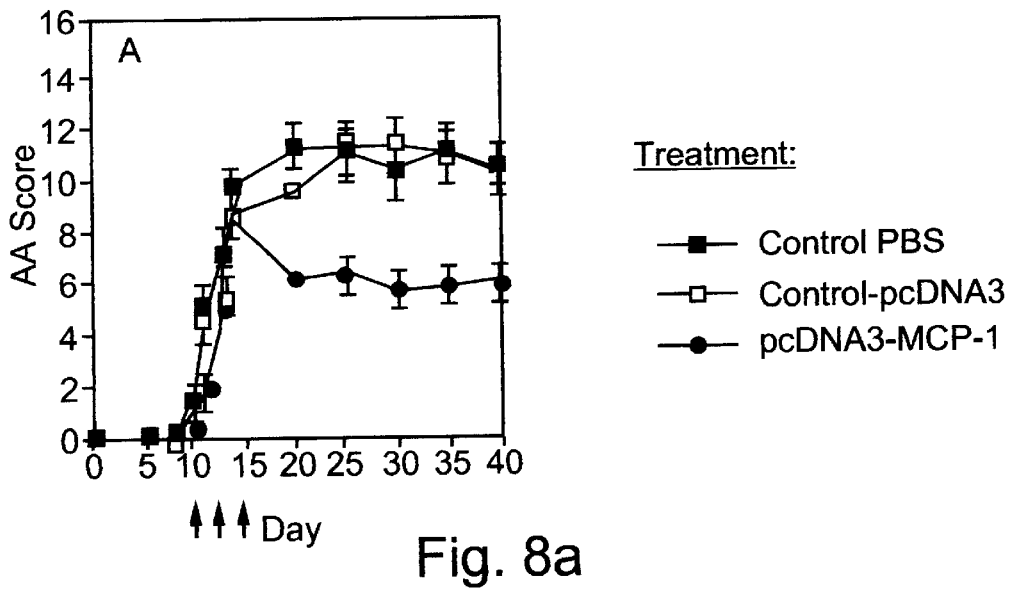
Figures 8B, 8C:
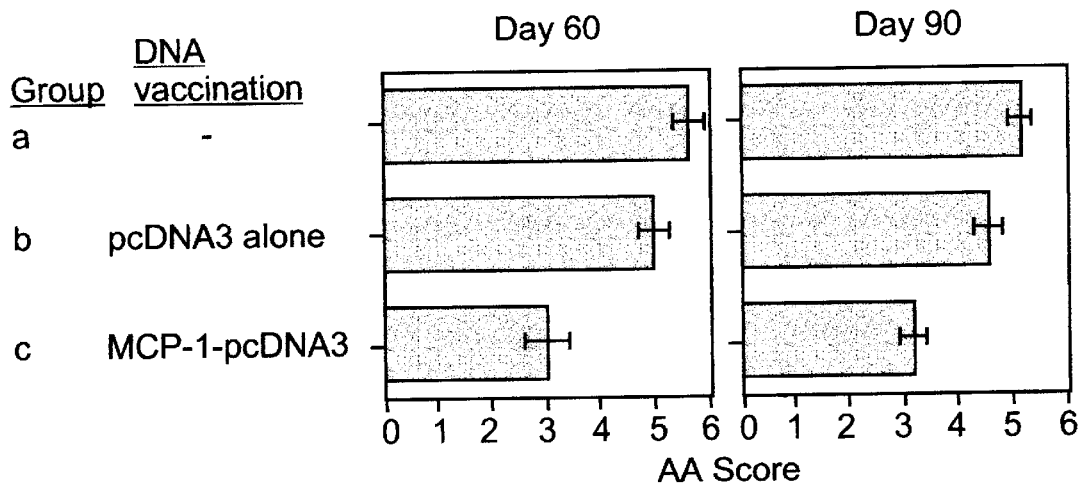

FIGS. 8a–c depict AA scoring of rats immunized with CFA to induce active AA and then randomly separated into three groups of twelve rats each. At the onset of disease (day 10), and on days 12 and 14 two of these groups were subjected to three repeated administrations of either the pcDNA3 vector (300 μg/rat) or the MCP-1 construct. The third group was inoculated with PBS. Results are shown as mean clinical score of 12 rats in each group ±SE.

Figure 9A:
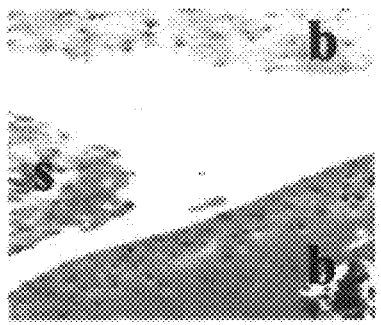
Figure 9B:
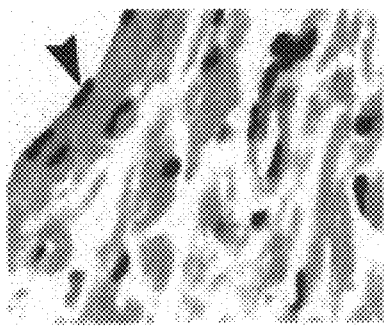
Figure 9C:
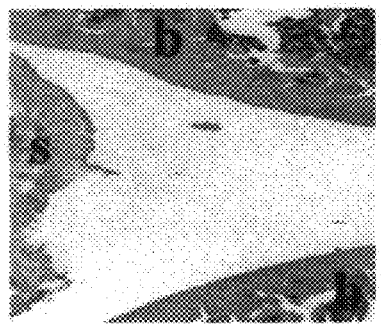
Figure 9D:
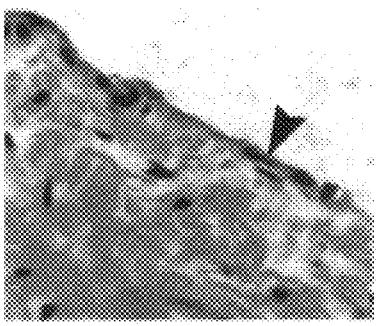
Figure 9E:
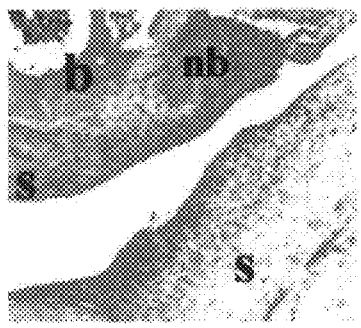
Figure 9F:
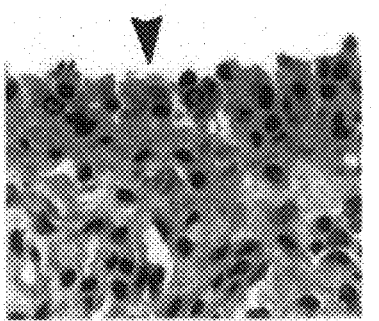
Figure 9G:
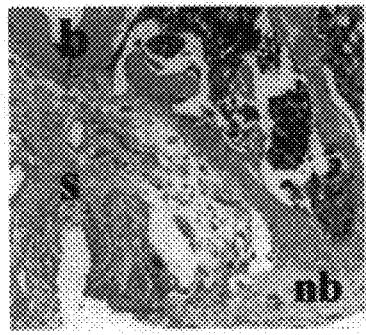
Figure 9H:
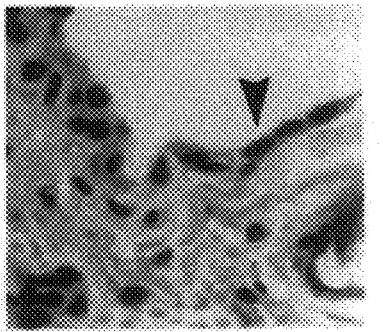
Figure 9I:
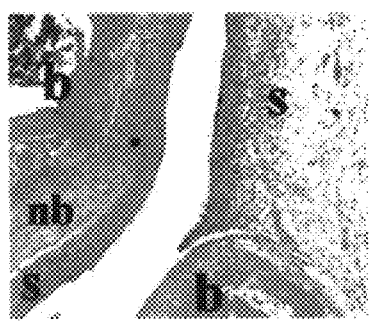
Figure 9J:
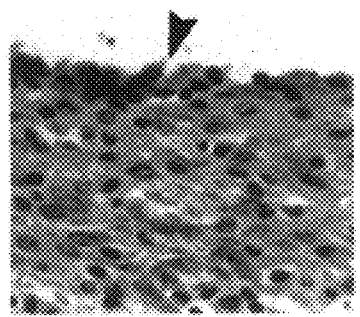
Figure 9K:
Figure 9L:
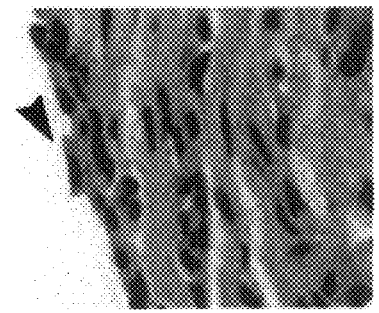
Figure 9M:
Figure 9N:
Figure 9O:
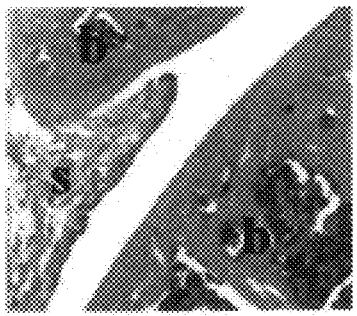
Figure 9P:
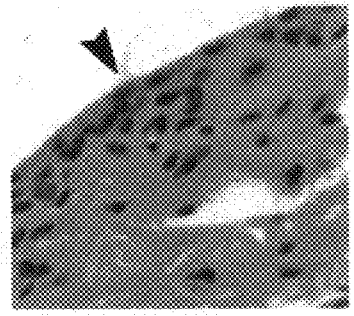

FIGS. 9a–p depict histological sections from joints of rats of each experimental groups described in Example 1. FIGS. 9a, c, e, g, i, k, m and o are magnified 5 times while FIGS. 9b, d, f, h, j, l, n and p are magnified 40 times. FIGS. 9a–d are sections from non-diseased joints taken from rats of an age which matches that of the diseased rats (9a–b day 30; 9c–d day 90); FIGS. 9e–f—joint sections taken 30 days following disease induction; FIGS. 9g–h—joint sections taken 90 days following disease induction; FIGS. 9i–j—joint sections from pcDNA3 treated rats, obtained 30 days following disease induction; FIGS. 9k–l joint sections from pcDNA3 treated rats, obtained 90 days following disease induction. FIGS. 9m–n—joint sections of MCP-1 treated rats, obtained 30 days following disease induction. FIGS. 9o–p joint sections of MCP-1 treated rats obtained 90 days following disease induction. The arrowheads point to the synovial lining (b=bone; nb=new bone formation; s=synovial membrane).

FIGS. 10a–d depict a clinical score and the differences in leg swelling for groups of 12 Lewis rats which were exposed to four weekly administrations of TNF-α DNA vaccine. Control rats were injected with either β-actin construct, the pcDNA3 vector alone, or with PBS. Three weeks alter the last immunization all rats were immunized with CFA to induce active AA. Results are shown as mean of 12 rats (days 10–30), or 8 rats (day 31-on) ±SE.

FIGS. 11a–c depict the breakdown of tolerance to self in DNA vaccinated rats. FIG. 11a depicts a comperative analysis of self-specific antibody titer to TNF-α developed in each group on day 20. FIG. 11b follows the kinetics of self specific antibodies to TNF-α generated following administration of CFA to induce a local DTH response, or chronic AA. FIG. 11c follows the kinetics of self specific antibodies to TNF-α generated following administration of CFA to induce a local DTH response, or chronic AA in DNA vaccinated rats. Results are shown as mean of three different serum samples ±SE.

Figure 12:
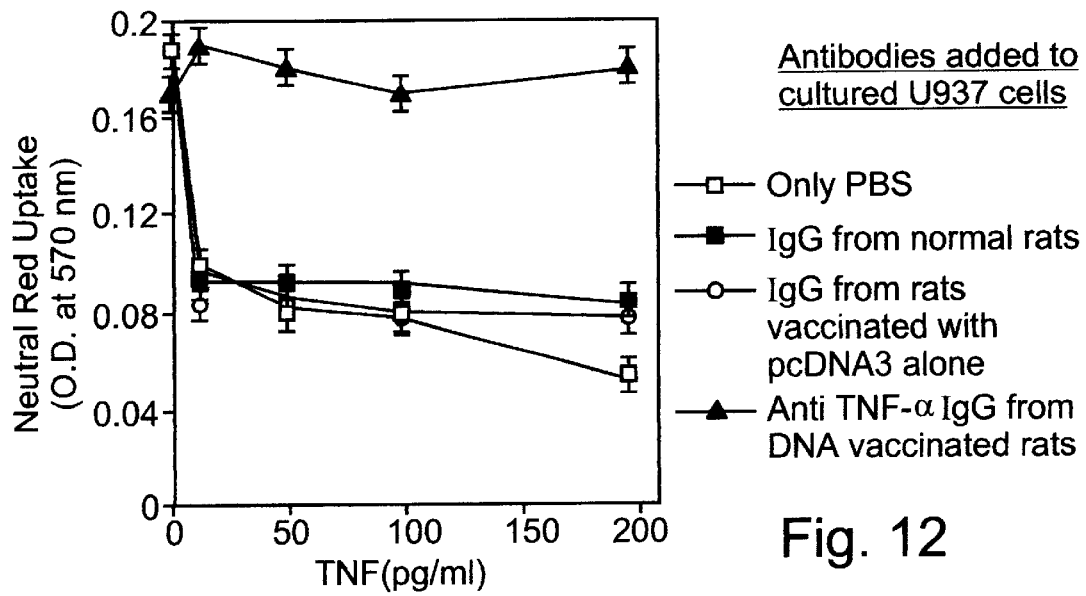

FIG. 12 depicts the ability of a CNBr purified IgG fraction of TNF-α specific neutralizing antibodies purified from sera of rats that were previously vaccinated with TNF-α naked DNA vaccine to inhibit neutral red uptake of U937 cells. IgG purified from normal rat serum (100 μg/well). IgG fraction from pcDNA3 vaccinated EAE rats (100 μg/well) or an equal volume of PBS were used as controls. Results are shown as mean optical density (OD) at 570 nm ±SE.

Figure 13:
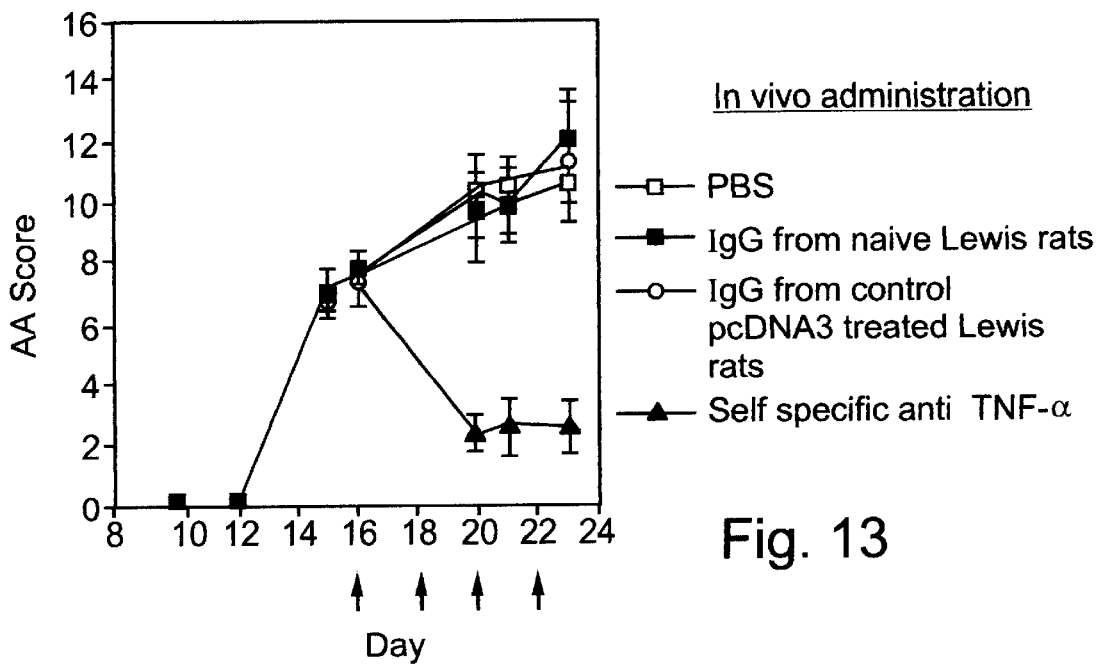

FIG. 13 depicts the clinical score of AA diseased rats challenged with TNF-α antibodies produced by previous DNA vaccination experiments. Four groups of six rats each were immunized with CFA to develop poly-arthritis. Beginning on day 16 AA rats were challenged intravenously (i.v.) every other day, with 100 μg of TNF-α antisera. Results are shown as mean clinical score of six rats in each group ±SE.

Figure 14:
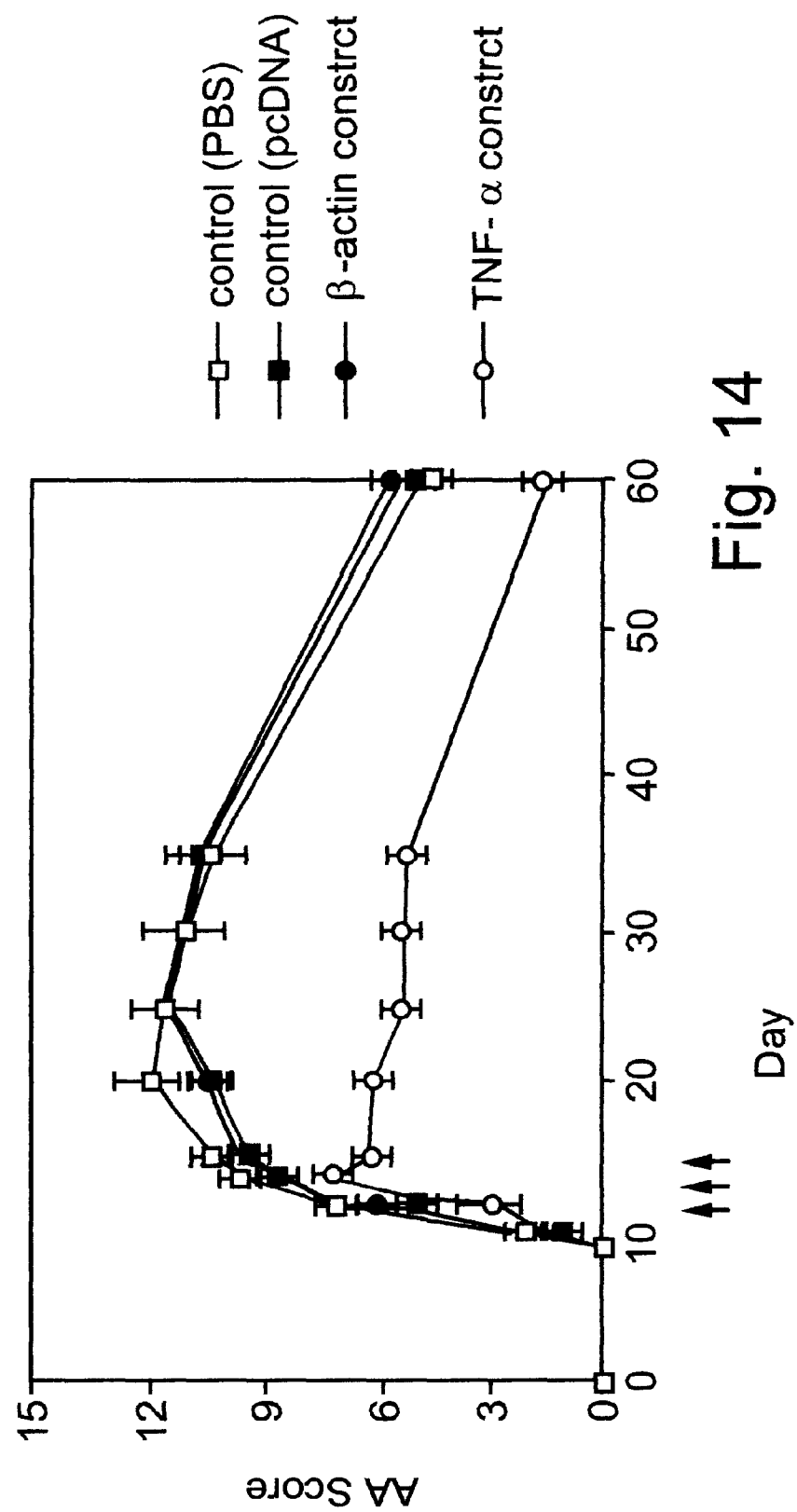

FIG. 14 depicts the clinical score of diseased rats treated with various vaccine compositions. Lewis rats were immunized with CFA to induce active AA and then randomly separated into four groups of twelve rats each. At the onset of disease (day 10), and on days 12 and 14 two of these groups were subjected to three repeated administrations of either a control (β-actin construct, pcDNA3 or PBS), or the TNF-α construct. Results are shown as mean clinical score of 12 rats in each group ±SE.

Figure 15A:
Figure 15B:
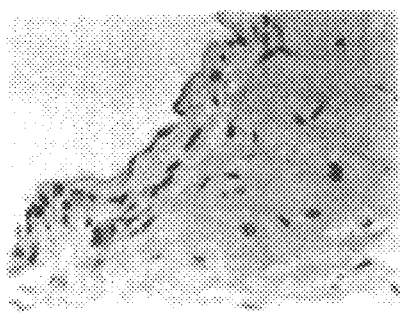
Figure 15C:
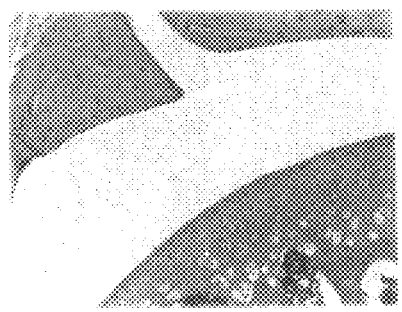
Figure 15D:
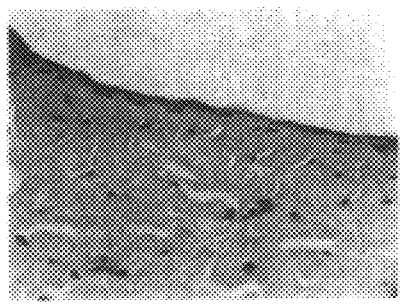
Figure 15E:
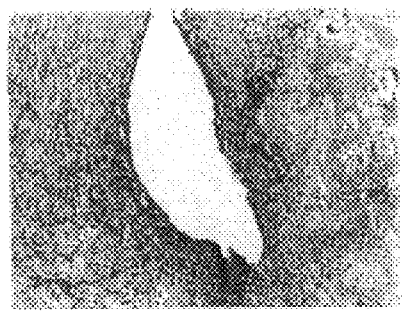
Figure 15F:
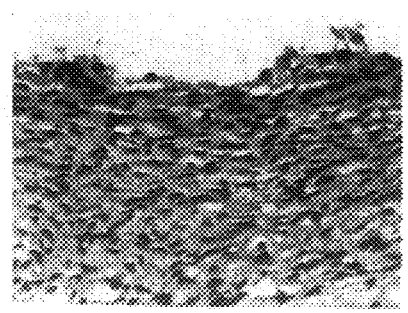
Figure 15G:
Figure 15H:
Figure 15I:
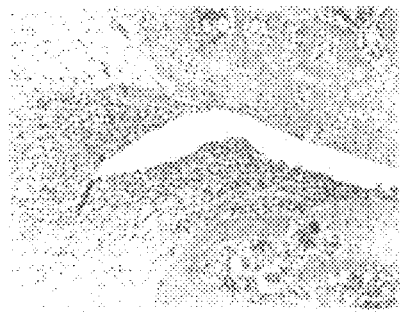
Figure 15J:
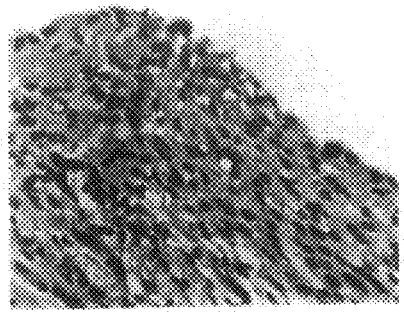
Figure 15K:
Figure 15L:
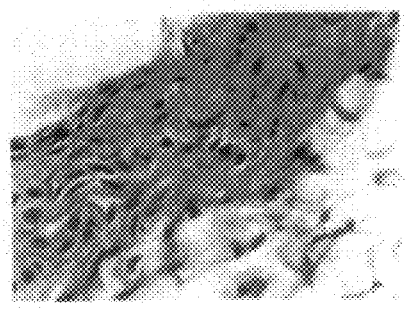
Figure 15M:
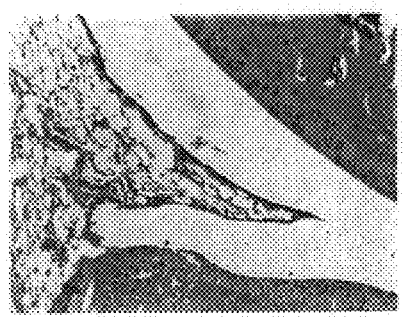
Figure 15N:
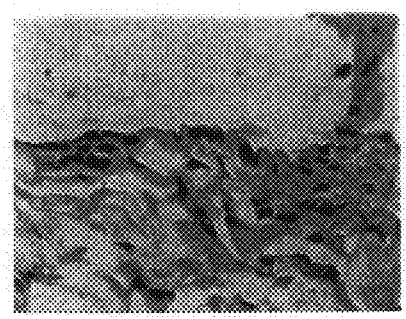
Figure 15O:
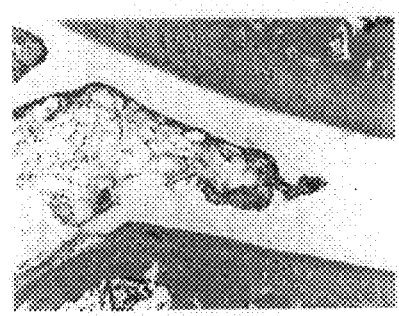
Figure 15P:

FIGS. 15a–p depict histological sections of rat joints. FIGS. 15a, c, e, g, i, k, m and o are magnified 10 times. while FIGS. 15b, d, f, h, j, l, n and p are magnified 40 times. FIGS. 15a–d depict non-diseased joint sections taken from rats of an age which matches that of the diseased rats (15a–b day 30; 15c–d day 60). FIG. 15e–f—joint sections taken 30 days following disease induction; FIGS. 15g–h—joint sections taken 90 days following disease induction; FIGS. 15i–j—joint sections taken 30 days following disease induction; FIGS. 15k–i—joint sections taken 60 days following disease induction; FIGS. 15m–n—joint sections of TNFα treated rats taken 30 days following disease induction; FIGS. 15o–p—joint sections of TNF-α treated joints taken 60 days following disease induction. The arrowheads point to the synovial lining (b=bone; nb=new bone formation; s=synovial membrane).

DESCRIPTION OF THE PREFERRED EMBODIMENTS

The present invention is of pharmaceutical compositions and methods utilizing same which can be used to treat an individual suffering from rheumatoid arthritis. Specifically, the present invention can be used to elicit the formation of immunoglobulins directed at cytokines, preferably chemokines, to thereby induce the breakdown of self-tolerance to these cytokines/chemokines and inhibit the progression of the disease.

The principles and operation of the present invention may be better understood with reference to the drawings and accompanying descriptions.

Before explaining at least one embodiment of the invention in detail, it is to be understood that the invention is not limited in its application to the details set forth in the following description or illustrated in the drawings. The invention is capable of other embodiments or of being practiced or carried out in various ways. Also, it is to be understood that the phraseology and terminology employed herein is for the purpose of description and should not be regarded as limiting.

According to the present invention there is provided a method of treating rheumatoid arthritis of an individual. As used herein the term "treating" implies either to ameliorating or arresting the progression of rheumatoid arthritis. In any case, treatment of the individual substantially reduces symptoms manifested by both clinical and histological findings.

According to one aspect of the present invention, DNA vaccination is used for exposing the individual to an immunologically recognizable portion of a cytokine in an amount sufficient to induce a formation of anti-cytokine immunoglobulins.

As used herein the phrase "immunologically recognizable portion" refers to a stretch of at least 6, preferably 8 or more amino acids, e.g., the entire sequence, either contiguous or not, which is capable of inducing an immunological response against itself when expressed from exogenous DNA by cells of the individual. The phrase "antigenic epitope" refers to a single antigenic determinant.

As used herein and in the claims, the term "immunoglobulin" refers to any of several classes of structurally related proteins that function as part of the immune response of the individual, which proteins include IgG, IgD, Ig, IgA, IgM and related proteins. Preferably, as used herein the term immunoglobulin refers to the IgG and IgM classes.

The anti-cytokine immunoglobulins formed in the individual serve to neutralize or ameliorate an activity of a respective and/or cross reactive endogenous cytokine which is responsible for the immobilization of T-lymphocytes to the site of inflammation in the joint of arthritic individuals. As such, neutralizing or ameliorating the activity of these endogenous cytokines enables to treat rheumatoid arthritis.

According to preferred embodiments of the present invention the immunologically recognizable portion of the cytokine to which the individual is exposed can be derived from TNF-α or alternatively it can be derived from a chemokine, preferably a C—C chemokine, such as, but not limited to, MIP-1α, MCP-1, MIP-1β or RANTES.

It will be appreciated that the immunologically recognizable portion can include a consensus amino acid sequence shared by several cytokines. The use of such a consensus sequence is particularly advantageous since it can generate immunoglobulins which are cross reactive with several types of cytokines, thereby further enhancing the capability of the method of the present invention in treating rheumatoid arthritis. Suitable amino acid alignment software (e.g., the GCG software) can be used by the ordinary artisan to align the primary amino acid sequences of several chemokines and to thereby identify consensus amino acid sequences shared thereby. A reverse translated polynucleotide can than be prepared accordingly using solid phase technology and be tested as a DNA vaccine as is further described herein. Additionally, immonogenicity, immunoreactivity, and cross reactivity a consensus sequence towards cytokines can be studies using conventional immunization procedures an immunoassays.

According to the present invention, the individual is exposed to the immunologically recognizable portion of the cytokine via one of several methods. Which result in in-vivo or ex-vivo transformation of cells with an exogenous polynucleotide which codes for the immunologically recognizable portion of a cytokine.

Ex-vivo transformation of the exogenous polynucleotide into cells is accomplished by any conventional method for transfection, infection or the like as is well known in the art. Such cells are preferably collected from the individual to be treated so as to serve for subsequent autologous implantation thereof back into the individual. In-vivo transformation is effected by one of several ways, as further detailed hereinunder.

Thus, according to one aspect of the present invention, an exogenous polynucleotide encoding the immunologically recognizable portion of a cytokine is administered and expressed within cells of the individual in-vivo. According to this method the expression level of the exogenous polynucleotide is sufficient to induce a formation of anti-cytokine immunoglobulins.

According to preferred embodiments of the present invention, the exogenous polynucleotide encoding the immunologically recognizable portion of a cytokine is preferably DNA in a form of, or contained in, a nucleic acid construct, which also includes regulatory sequences, such as a promoter, an enhancer a terminator and the like which are functional in eukaryotic cells, preferably mammalian cells. For example, the exogenous polynucleotide can be contained in plasmid, retroviral vector, adenoviral vector, vaccinia viral vector, herpes viral vector, lenti virus vector, EBV vector, CMV vector, polio virus vector, sindbis viral vector, semliki forest virus vector, parvo virus vector, adeno-associated virus vector, or virus like particle (VLP) vector. Alternatively, the exogenous polynucleotide can be in the form of RNA.

The nucleic acid construct including the exogenous polynucleotide can be administered to the individual as a part of a pharmaceutical composition which includes a pharmaceutically acceptable carrier such as, but is not limited to, a physiological solution, a viral capsid carrier, a liposome carrier, a micelle carrier, a complex cationic reagent carrier, a polycathion carrier such as poly-lysine and a cellular carrier. Further description of some of these pharmaceutically acceptable carriers, pharmaceutical composition preparation and of method of administering such compositions are detailed hereinbelow.

Hereinafter, the phrase "pharmaceutically acceptable carrier" refers to a carrier that does not cause significant irritation to an organism and does not abrogate the biological activity and properties of the administered active compound. An adjuvant is included under this definition.

According to another aspect of the present invention the method of treating rheumatoid arthritis in an individual can be effected by administering to the individual cells expressing, from an exogenous polynucleotide, at least an immunologically recognizable portion of a cytokine. This method is similar to that described above with the exception that the administration of the exogenous polynucleotide is perfomed ex-vivo.

According to this aspect of the present invention, the exogenous polynucleotide which is preferably included within the nucleic acid construct, is used to transform cells, either stably (integration into the genome) or transiently (expression in the nucleus or cytoplasm without genomic integration). Suitable cells include, but are not limited to, dendritic cells, macrophages, B cells or fibroblasts, which are preferably taken from the individual or from an individual which is immunogenically related to the individual. Methods of isolating, ex-vivo culturing, transforming and retransplating such cells are well known in the art, see, for example, "Culture of Animal Cells—A Manual of Basic Technique" by Freshney, Wiley-Liss, N.Y. (1994), Third Edition.

According to another preferred embodiment of the present invention, the transformed cells secrete the cytokine polypeptide expressed from the exogenous polynucleotide. In this case, the exogenous polynucleotide also includes a sequence region which is in translational fusion to the cytokine coding region and which codes for a signal peptide for targeting the cytokine into the ER and thereafter out of the cell. Numerous examples to signal peptide coding sequences utilizable by this aspect of the present invention are known in the art and as such no further description is given herein. In particular, such sequences can be derived from the cytokines themselves, all of which are secreted proteins.

According to another preferred embodiment of the present invention, the transformed cells are antigen presenting cells. As such these cells present or display portions of the cytokine following the expression thereof by the cell. It will be appreciated that the portions displayed preferably include antigenic epitopes which elicit a strong antigenic response when such cells are administered to the individual.

There is increasing evidence indicating that an immunogenic response is stronger when peptides are presented or displayed on antigen presenting cell (Mayordomo et al. (1995) Nature Med. 1, 1297–1302). The most common cells used to present antigens are bone marrow and peripheral blood derived dendritic cells (DC).

Thus the methods described above utilize the expression of an immunogenic portion of a cytokine, preferably a chemokine within an individual in order to induce the breakdown of immunogenic tolerance to the cytokine thereby inhibiting the progression of the disease.

Although the above described methods are presently preferred, expression within the individual of a variable portion of the light and/or heavy chains of an immunoglobulin which was generated against a cytokine responsible for the mobilization of T-lymphocytes to a site of arthritic inflammation, can also be utilized to inhibit the progression of the disease.

Thus, according to yet another aspect of the present invention, there is provided a method of treating rheumatoid arthritis in an individual. The method according to this aspect of the present invention is effected by expressing within the individual an exogenous polynucleotide encoding at least a portion of a variable region of an anti-cytokine immunoglobulin. The variable region can be of either the light and/or the heavy chains of the immunoglobulin. According to this aspect of the present invention the variable region of the anti-cytokine immunoglobulin is expressed within the individual in a level sufficient for neutralizing or ameliorating the activity of a respective and/or cross reactive endogenous cytokine, to thereby treat rheumatoid arthritis.

It will be appreciated that such an expression can be effected as described above by either in-vivo or ex-vivo transformation of cells. It will further be appreciated that in any case secretion of the variable region of an anti-cytokine immunoglobulin is preferred. Such secretion can be effected as described above for another aspect of the present invention.

Cloning of cDNA encoding an antibody or fragments thereof may be accomplished by several approaches known in the art. In the preferred approach, mRNA from clonal hybridoma cell lines which produce an antibody active against a cytokine is employed as starting material. The cells are harvested and mRNA is extracted by standard methods known in the art. The cDNA is prepared by reverse transcription of the mRNA by standard methods known in the art. The cDNA for each chain of the immunoglobulin is cloned separately, and may be amplified by polymerase chain reaction using appropriate primers. The cDNA is then ligated into appropriate vectors by standard methods. The cDNA may be cloned into any suitable vector and either directly administered into the individual (in-vivo method) or used to transform cell (ex-vivo method). cDNAs encoding the variable regions of light and heavy chains can be ligated in an in frame spaced orientation so as to encode for an active single chain antibody.

The exogenous polynucleotide encoding the variable region of an anti-cytokine immunoglobulin can be combined with any suitable pharmaceutically acceptable carrier so as to form a pharmaceutical composition as described above.

The exogenous polynucleotide or polynucleotide expressing cells according to the various aspects of the present invention which constitute the "active ingredient" of the pharmaceutical composition can be administered to the individual via various administration modes.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, inrtaperitoneal, intranasal, or intraocular injections.

Alternately, one may administer a preparation in a local rather than systemic manner, for example, via injection of the preparation directly into a vascularized region close to the arthritic joint of the individual.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredient may be formulated in aqueous solutions, preferably in physiologically compatible buffers such as Hank's solution. Ringer's solution, or physiological salt buffer. For transmucosal administration, penetrants appropriate to the barrier to be permeated are used in the formulation. Such penetrants are generally known in the art.

For oral administration, the active ingredient can be formulated as tablets, pills, dragees, capsules, liquids, gels, syrups, slurries, suspensions, and the like, for oral ingestion by a patient.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredient is conveniently delivered in the form of an aerosol spray presentation from a pressurized pack or a nebulizer with the use of a suitable propellant, e.g., dichlorodifluoromethane, trichlorofluoromethane, dichlorotetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continues infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active ingredient in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of rheumatoid arthritis.

Determination of a therapeutically effective amount is well within the capability of those skilled in the art, especially in light of the detailed disclosure provided herein.

For any preparation used in the methods of the invention, the therapeutically effective amount or dose can be estimated initially from in-vitro and cell culture assays. For example, a dose can be formulated in animal models to achieve a desired circulating antibody concentration or titer. Such information can be used to more accurately determine useful doses in humans.

Toxicity and therapeutic efficacy of the active ingredients described herein can be determined by standard pharmaceutical procedures in-vitro, in cell cultures or experimental animals. The data obtained from these in-vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

Dosage intervals can also be determined using the MEC value. Preparations should be administered using a regimen, which maintains plasma levels above the MEC for 10–90% of the time, preferable between 30–90% and most preferably 50–90%.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Thus, the present invention provides pharmaceutical compositions and methods for treating rheumatoid arthritis in an individual.

As is further detailed in the Examples section below, the study conducted while reducing the present invention to practice utilized intrabody expression of TNF-$\alpha$, MCP-1, MIP-$\alpha$, MIP-1$\beta$ and RANTES which led to a breakdown in immunological tolerance to the product of each gene of interest and establishment of an immunological memory. As is further demonstrated by this present study, the establishment of immunological memory facilitated recovery from arthritis in a rat inflicted with chronic arthritis. The findings of this study further indicate that the MCP-1 naked DNA vaccine is highly effective in inhibiting the development and progression of AA, as determined by clinical scoring, measurements of limb swelling, and histological analysis.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I–III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1–4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I–III Cellis, J. E., ed. (1994); "Current Protocols in Immunology" Volumes I–III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example. U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthes is" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1–317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL press (1996); all of which are incorporated by reference as if fully set forth herein. Other general references are provided throughout this document. The procedures therein are believed to be well known in the art and are provided for the convenience of the reader. All the information contained therein is incorporated herein by reference.

Material and Experimental Methods

Rats: Female Lewis rats, approximately six weeks old were purchased from Harlan (Jerusalem, Israel) and maintained under clean conditions in our animal facility.

Immunizations and active disease induction: Rats were immunized subcutaneously in the base-tail with 0.1 ml of CFA (incomplete Freund's adjuvant supplemented with 10 mg/ml heat-killed *Mycobacterium tuberculosis* H37Ra in oil, Difco laboratories Inc., Detroit, Mich.). Rats were then monitored for clinical signs daily by an observer blind to the treatment protocol as we described elsewhere (Lider et al., 1987). Severity of the disease was quantified by scoring each limb on a scale of 0–4 which indicate the severity of peripheral joint swelling and erythema: 0=no signs of disease, 1=disease evident in a small number of distal joints of the limb, 2=disease evident in all of distal joints of the limb, 3=disease evident in all the limb, 4=severe disease evident in all the limb. The arthritic clinical score was determined as the sum of the scores of all four limbs from each animal (0–16). The degree of arthritis, indicated by swelling, was quantified by measuring front and hind limb circumference using a caliper (Lange Skinfold Caliper, Cambridge Scientific Industries, Cambridge, Mass.). Measurements were taken at three time points during the course of disease: days 20, 60 and 90. They are presented as the average of the difference between swelling diameter of treated joints and healthy ones.

DNA vaccination: First strand cDNA was then subjected to 35 cycles of PCR amplification using specific oligonucleotide primers which were designed based on the published sequence of each chemokine (NCBI Accession Numbers: Rat MIP-α-U06435, Rat MIP-1β-U06434, Rat RANTES-U06436 and Rat MCP-1 M57441), and rat TNF-α (NCBI Accession Number m63122), as follows: Rat MIP-1α (sense) 5'-ATGAAGGTCTCCACCACTGCCCTTGC-3' (SEQ ID NO:1); Rat MIP-1αα (antisense) 5'-TCAGGCATTCAGTTCCAGCTCAGTG-3' (SEQ ID NO:2); Rat MIP-1β (sense) 5'-ATGAAGCTCTGCGTGTCTG CCTTC-3' (SEQ ID NO:3); Rat MIP-1β (antisense) 5'-TCAGTTCAACTCCAAGTCATTCAC-3' (SEQ ID NO:4); Rat RANTES (sense) 5'-ATGAAGATCTCTGCAGCTGCATCC-3' (SEQ ID NO:5); Rat RANTES (antisense) 5'-CTAGCTCATCTCCAAATAGTTG-3' (SEQ ID NO:6); Rat MCP-1 (sense) 5'-ATGCAGGTCTCTGTCACGCTTCTGGGC-3' (SEQ ID NO:7); Rat MCP-1 (antisense) 5'-CTAGTTCTCTGTCATACTGGTCAC-3' (SEQ ID NO:8); Rat TNF-α (sense) 5'-ATGAGCACAGAAAGCATGAT-3' (SEQ ID NO:9); and Rat TNF-α (antisense) 5'-TCACAGAGCAATGACTCCAAA-3' (SEQ ID NO:10).

Sequenced PCR products of rat MIP-1α, MCP-1, MIP-1β, RANTES and TNF-α were transferred into a pcDNA3 vector (Invitrogen, San Diego, Calif.). In addition cDNA encoding rat β-actin has been obtained using specific oligonucleotide primers (sense 5'-ATGGATGACGATATCGCTGCGCTC-3' (SEQ ID NO:11); anti-sense 5'-CTACCGGCCAGCCAGACG-3' (SEQ ID NO:12). Following cloning and sequence verification the above cDNA was ligated into the pcDNA3 vector to be used as a control DNA vaccine.

Large scale preparation of plasmid DNA was conducted using Mega prep (Qiagen Inc., Chatsworth, Calif.). Cardiotoxin (Sigma, St. Louis. Mo.) was injected into the tibialis anterior muscle of 6–8 week old female Lewis rats (10 μM per leg). Five days following the toxin injection rats were injected with 100 μg DNA in PBS. Four-five days after the first immunization one rat from each group was sacrificed and transcription of the relevant chemokine was verified using RT-PCR on tibialis anterior muscle samples. Thereafter, naked DNA vaccines were given four times with intervals of 6–7 days between each injection.

Purification of antibodies: Antibodies from rat sera were purified using a High-Trap Protein G column (Pharmacia, Piscataway, N.J.) according the manufacturer's protocol. Then antibody titer to various chemokines was determined by an ELISA assay as described below.

CNBr Purification of C—C chemokine specific antibodies: Before being tested for their in-vivo characteristics (i.e. ability to affect the course of AA) sera from all DNA vaccinated rats were purified. Commercially available recombinant MCP-1, MIP-1α, MIP-1β, RANTES all from chemicon or TNF-β from Genzyme (Cambridge, Mass.) were bound to a CNBr activated Sepharose Column according to the manufactures instructions (Pharmacia biotech, catalog number 17-0820-01). Specific antibodies to the gene product of each DNA vaccine were (IgG fraction) loaded on the columns, each consisting the appropriate commercially available C—C chemokine gene product bound to CNBr, and then eluted by an acidic elution buffer (glycine pH 2.5). Isotype determination of the purified antibody (ELISA) revealed that purified antibodies are mostly of the IgG2a Isotype.

In-vitro chemotaxis assay for MIP-1α, MCP-1, MIP-1β, RANTES: In-vitro chemotaxis assay was conducted as previously described (Youssef et al., 1998). The assay is based on (Luo et al., 1994) with minor modifications. Peritoneal macrophages were isolated as previously described (Luo et al., 1994) and suspended in DMEM enriched with 1% BSA. Cell migration was evaluated in standard Boyden chambers (Neuroprobe, Cabin John, Md.). Macrophages ($1.2 \times 10^6$ cells) were aidded to the upper well. Chemotactic factors: fMLP (Sigma, $10^{-7}$ M) rat recombinant MIP-1α (Chemicon International, Temecula, Calif. 200 ng/ml) or rat recombinant MCP-1 (Chemicon International, Temecula, Calif. 100 ng/ml) or rat recombinant RANTES (Chemicon International, Temecula, Calif. 100 ng/ml) or human recombinant MIP-1β (Chemicon International, Temecula, Calif. 100 ng/ml) were added to the lower wells, with, or without pre-incubation with the required antibodies (10 μg/well) at 37° C. for 30 minutes. Migration was allowed to proceed for 90 minutes at 37° C. The polycarbonate tilters. 5 μm pore size, (Osmonics, Livermore, Calif.) were removed and stained with Diff-Quik (Dade AG, Dudingen, Switzerland). Five ×400 fields were selected randomly on each filter and the number of migrating cells was counted.

Determination of the neutralizing activity of TNF-α specific antibodies: Determination of the neutralizing activity of TNF-α specific antibodies was performed as described in detail elsewhere (Wallach, 1984), with the modification of using the U937 monocyte cell line (ATCC CRL-1593.2), at a concentration of 4×104 cells/well, as a target cell for the assay (Wildbaum and Karin, 1999).

Evaluation of anti-cytokine/chemokine antibody titer in sera of DNA vaccinated rats: A direct ELISA assay has been utilized to determine the anti-C—C chemokine antibody titer in DNA vaccinated rats. ELISA plates (Nunc, Roskilde, Denmark) were coated with 50 ng/well commercially available recombinant rat RANTES, MIP-1α, MCP-1 or human MIP-1β (Chemicon International, Temecula, Calif.) or TNF-α (Genzyme, Cambridge. Mass.). Sera from DNA vaccinated rats were added in serial dilutions from $2^5$ to $2^{30}$ to wells that were, or were not, previously coated with each chemokine. Calculation of each titer was done by comparing the OD measured in wells coated with the relevant chemokine to those not coated with this chemokine. Goat anti-rat alkaline phosphatase conjugate IgG antibodies (Sigma) were used as a labeled antibody. p-Nitrophenyl Phosphate(p-NPP) (Sigma) was used as a soluble alkaline phosphatase substrate. Results of triplicates were calculated as log 2 antibody titer ±SE.

Histopathology: Joints were removed at various time points following disease induction, fixed with 10% buffered formalin, decalcified in 5% ethylenediaminetetraacetic acid in buffered formalin, embedded in paraffin and sectioned along the midline through the metatarsal region (Bacha el al., 1992). Sections were stained with hematoxylin and eosin and analyzed by a histopathologist who was a blind observer to the experimental procedure. Evaluation was made based upon inflammatory mononuclear cell infiltrate in the synovial membrane, thickness of the synovial lining, joint space narrowing and periosteal new bone formation. Clinical score was determined as follows: 0=no evidence of disease, 1=mild lymphocytic infiltrate, 2=widespread mononuclear of inflammation and thickening of the synovial lining and 3=severe bone destruction, new bone formation and destruction of the synovial lining (Bacha el al., 1992).

Statistical analysis: Significance of differences was examined using Student's t-test. A value of P<0.05 was considered significant. One way multiple range ANOVA test with significance level of p<0.05 was performed for multiple comparisons of antibody titers to various C—C chemokines in naked DNA vaccinated rats.

EXAMPLE 1

Results of Experiments conducted with the chemokines MIP-1α, MCP-1, MIP-1β, and RANTES Prevention of AA using Naked DNA Vaccines:

Cloned PCR products of the MIP-1α, MCP-1, MIP-1β, RANTES C—C chemokines (Youssef et al., 1998) were ligated into a pcDNA3 mammalian expression vector and used as constructs for naked DNA vaccination (FIG. 1a). Lewis rats were exposed to four weekly administrations of various naked DNA vaccines. Control rats were either injected with the pcDNA3 vector alone, or with PBS. Three weeks after the last immunization all rats were immunized with CFA to induce AA. Under working conditions established in the present study, AA manifests a long lasting form of disease that includes an acute phase, peaking around day 20, and a chronic phase that persists for more than 100 days (FIG. 1a). All control (PBS immunized) and pcDNA3 vaccinated rats (10 per group) developed a severe form of disease with a maximal clinical score (day 20) of 11±1.39 and 10±1.1 respectively (FIGS. 1a–b). At this time each one of the four chemokine DNA constructs led to a significant (p<0.01) reduction in disease severity (6.8±0.93, 5.1±0.7, 6±1.2 and 6.8±1.3 for treatment with MIP-1α, MCP-1, RANTES and MIP-1β accordingly) as determined by measuring the limb swelling (FIGS. 1b–d). Representative joint sections from all experimental groups (4 animals per group) were obtained on day 30 and screened for histological inflammatory mononuclear cell infiltrate in the synovial membrane, thickness of the synovial lining, joint space narrowing and periosteal new bone formation. Histological scores are summarized in (Table 1) below.

TABLE 1

Histological changes in AA rats as a response to DNA vaccination with C-C chemokines

| DNA vaccine | AA induction | Histological score |
|---|---|---|
| – | – | 0 |
| – | + | 3 ± 0[a] |
| pcDNA3 | + | 2.8 ± 0.18[a] |
| + MCP-1 | + | 0.83 ± 0.33[d] |
| + MIP-1α | + | 1.3 ± 0.23[c] |
| + MIP-1β | + | 2 ± 0.28[b] |
| + RANTES | + | 1.5 ± 0.24[c] | p < 0.001 for the comparison between d and a, p < 0.05 for the comparison between d and b,
p < 0.00 for the comparison between c and a, p < 0.05 for the comparison between b and a.

Representative sections are presented in (FIGS. 2a–n). Sections obtained from C—C chemokine DNA vaccinated rats displayed a marked reduction in each of the above parameters as compared to control and pcDNA3 treated AA rats. Amongst the C—C chemokine DNA vaccinated rats those subjected to the MCP-1 DNA construct displayed the lowest histological score (table 1, histological score 0.83±0.33 compared to 2.8±0.18 and 3±0 in pcDNA3 or PBS treated rats p<0.001 respectively, and to 2.±0.28 in MIP-1β DNA vaccinated rats, p<0.05). Similarly MIP-1β and RANTES DNA vaccines profoundly reduced the histological score of disease (histological score 1.3±0.23 and 1.5±0.24, p<0.001 compared to pcDNA3 or PBS treated rats). The effect of MIP-1β DNA vaccine on the above parameters was moderate (histological score 2±0.28 p<0.05 compared to pcDNA3 or PBS treated rats).

During the chronic phase of disease, in parallel to the above histological evaluation, the MCP-1 encoding DNA vaccines exerted the most significant effect on disease recovery (FIGS. 1c–d, p<0.001 as compared to control, pcDNA3 or MIP-1β DNA vaccinated rats). The MIP1-α DNA vaccine also led to a highly significant decrease in the long term clinical manifestation of disease (FIGS. 1c–d. p<0.01 as compared to control, pcDNA3 or MIP-1β DNA vaccinated rats). RANTES DNA vaccine notably decreased the long term severity of disease (FIGS. 1c–d, p<0.05 as compared to control or pcDNA3 treated rats), whereas the MIP-1β DNA vaccine did not exhibit any significant effect on the clinical manifestation of disease at these times. Again the clinical effect of DNA vaccine was verified by measuring differences in limb swelling (FIGS. 1b–d). Thus, these results show that C—C chemokine DNA vaccines can be used effectively to prevent AA. The vaccine encoding MCP-1 is the most potent in inhibiting not only the acute but also the chronic phase of disease. These results motivated further exploration of the therapeutic potential of this vaccine.

Self-specific Antibodies Developed in DNA Vaccinated Rats are Neutralizing in-vitro and Capable of Transferring the Protective Effect of each Vaccine:

DNA vaccination can potentially elicit both cellular and humoral responses against products of a given construct (Donnelly et al., 1997; Fu et al., 1997; Tang et al., 1992; Ulmer et al., 1993; Ulmer et al., 1996). To assess the contribution of the humoral response to the tolerant state, DNA vaccinated AA rats were monitored for the production of self-specific antibodies to the gene product of each DNA vaccine. Antibodies produced were evaluated for their ability to neutralize chemokine-mediated chemoattraction of leukocytes (in-vitro) and to interfere in the development of AA in adoptive transfer experiments.

Thus. Lewis rats were subjected to administration of various C—C chemokine DNA constructs, as described hereinabove. Three weeks later these rats were separated to sub-groups that were immunized with CFA either by a foot pad injection to induce a local DTH response or by a tail-base administration to induce poly-arthritis. Around the peak of the acute phase of disease the appearance of anti-self antibody in the serum was determined. Rats developing poly-arthritis manifest a notable self-specific antibody titer to the proinflammatory chemokine.

Figure 5A:
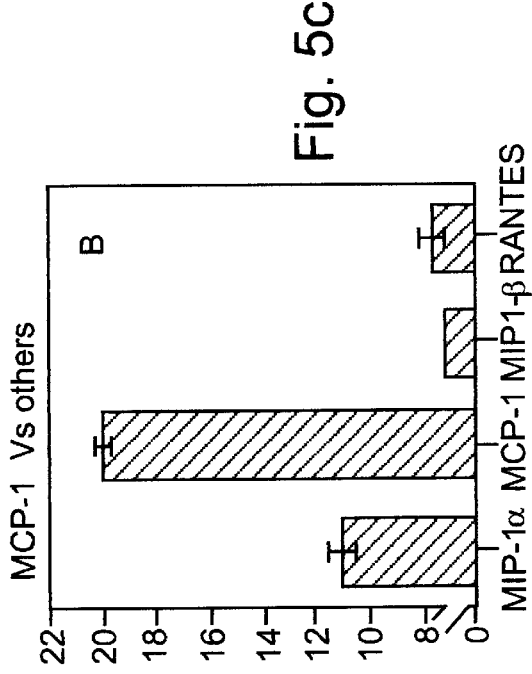
Figure 5C:
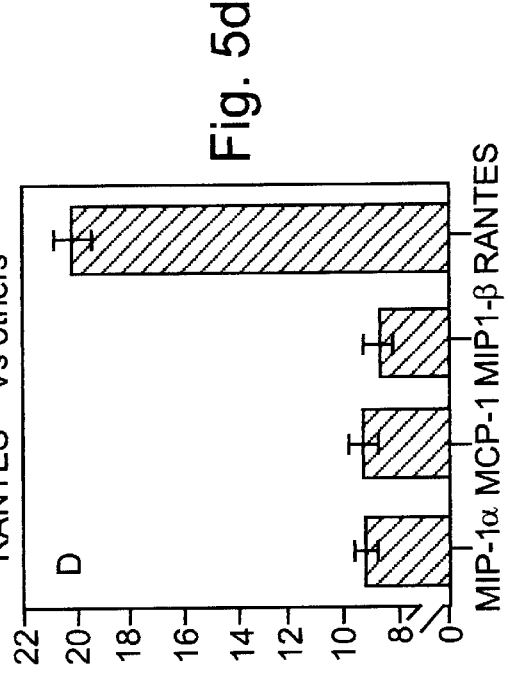
Figure 5B:
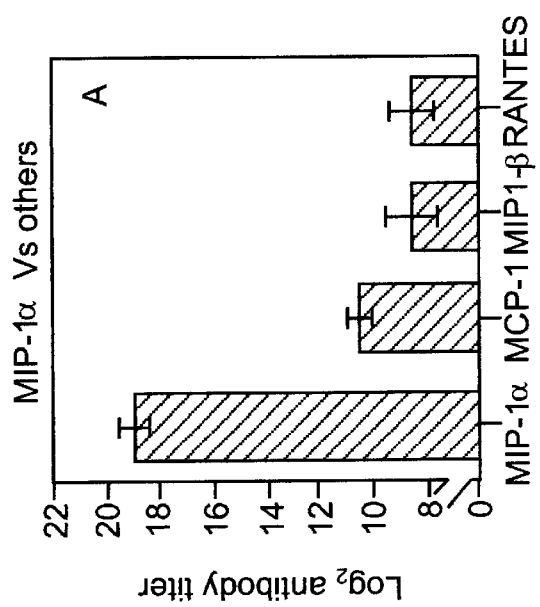
Figure 5D:
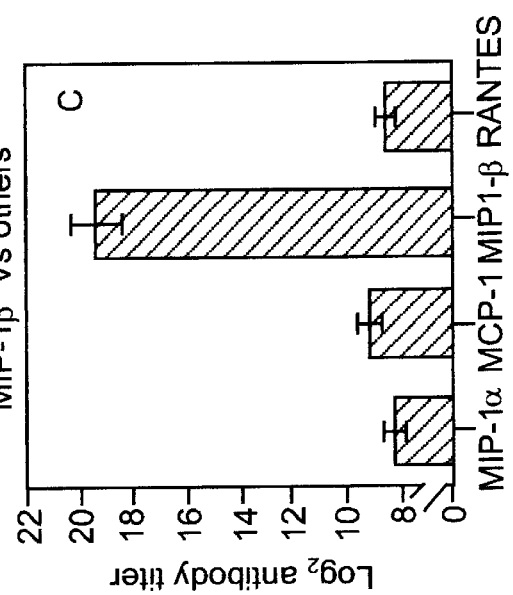

The results clearly show that even without DNA vaccination a notable antibody titer to each chemokine of interest could be observed in AA rats (FIGS. 3a–d). Interestingly, these titers differed not only from those in non-diseased rats, but also from those immunized to manifest a local DTH response (for MCP-1 FIG. 3a $\log_2$Ab titer of 12±0.55 Vs 7.5±0.55, p<0.01; for MIP-1α FIG. 3b $\log_2$Ab titer of 11±0.33 Vs 8.5±0.33, p<0.05; for MIP-1β FIG. 3c $\log_2$Ab titer of 12±0.55 Vs 7.5±0.55, p<0.01, for RANTES FIG. 3d $\log_2$Ab titer of 11.25±0.55 Vs 8±0.55, p<0.05). This substantial increase in self-specific titer was certainly not enough to prevent the development and progression of the inflammatory condition in AA (FIGS. 1a–d). Naked DNA vaccination, however, elicited the production of high titers of self specific antibody to the gene product of each given vaccine during the course of AA (FIGS. 3a–d $\log_2$ Ab titer of 20±0.55, 19±0.33, 19.5±0.55 and 20±0.47 for MCP-1, MIP-1α, MIP-1β and RANTES, p<0.001 for the comparison of each antibody titer to the titer developed in AA rats previously subjected to pcDNA3 alone or PBS), and depending on the inserted DNA construct, rendered DNA vaccinated rats a high state of AA resistance. The elevated titer to the product of each vaccinating construct continued to persist during the chronic phase of disease (FIGS. 4a–d), as did the clinical effect of these vaccines (FIGS. 1a–d). Since various C—C chemokines demonstrate similarities in amino acid sequence a possible cross-reactivity between antibodies produced in DNA vaccinated rats was examined. Sera from all antibody producing groups described in FIGS. 3a–d were examined for production of antibodies to each of the other C—C chemokines (FIGS. 5a–d). The results indicated that each DNA vaccinated group manifested a highly specific titer against homologous antigen: MCP-1, MIP-1α, MIP-1β and RANTES (FIGS. 5a–d, p<0.001 for the comparison of self-specific titer to each gene product compared to the other chemokines). MCP-1 DNA vaccinated rats, however, exhibited a notable cross reactive antibody titer against MIP-1α (FIG. 5b).

Antibodies were purified (IgG fraction, protein G purification) and evaluated for their competence to inhibit the migration of oil-induced peritoneal macrophages in a Boyden chemotaxis chamber assay, as previously described (Youssef et al., 1998). Self-specific antibodies generated in DNA vaccinated rats substantially blocked chemotaxis induced by each relevant chemokine (FIGS. 6a–d, p<0.01 for the comparison of the effect of anti-sera from DNA vaccinated rats to the effect of either medium, IgG from AA rats or IgG from AA rats previously exposed to pcDNA3 alone), and to a much lesser extent, if at all, chemotaxis induced by anti-sera from rats previously subjected to DNA vaccination with other C—C chemokine constructs. Although partial blockage of chemotaxis mediated by MIP-1α using anti-sera from MCP-1 DNA vaccinated rats was induced (FIG. 6d, p<0.05). The above effect could be attributed to the partial cross reactivity to MIP-1α in MCP-1 DNA vaccinated rats as shown in FIG. 5b, and as previously described by Youssef et al. (1998).

Thus, neutralizing antibodies generated in naked DNA vaccinated rats are chemokine specific. These antibodies were then evaluated for their competence to provide protection from severe ongoing AA (FIGS. 7a–b). Prior to being tested for their in-vivo characteristics (i.e. ability to affect the course of AA), sera obtained from all C—C chemokine DNA vaccinated rats were purified on Sepharose Columns, which included a C—C chemokine gene product bound to CNBr, as described hereinabove. Seven, ten & twelve days following the active induction of the disease, AA rats were challenged (i.v.) with 200 μg of each of these antibodies. Control rats were injected with either PBS, IgG from non-diseased rats. IgG from AA or from AA rats previously administered with pcDNA3 alone (FIGS. 7a–b). Repeated administration of neutralizing antibodies from MCP-1 and MIP-1α DNA vaccinated rats led to a marked reduction in disease severity as compared to all control groups. Day 16 mean maximal score of 6±0.5 and 5.8±0.65 was obtained in rats immunized with sera obtained form MCP-1 and MIP-1α vaccinated rats, as compared to 11±0.6, 9±0.7, 10±0.7 and 10±0.7 obtained for control AA rats treated with either PBS, IgG from AA rats, IgG from pcDNA3 vaccinated rats, or IgG from non-diseased rats (p<0.00 1 for the comparison of each experimental group to each of the three control groups).

Repeated administration of neutralizing antibodies from MIP-1β and RANTES DNA vaccinated rats led to a moderate decrease in disease severity (day 16, 7.8±0.9 and 7.8±0.9) which significantly differed (p<0.05) from the scores determined for each of the four control groups. Clinical scoring was also determined by measuring limb swelling and verified histologically (not shown).

These results may well explain in part the long lasting effect of C—C chemokine DNA vaccination in decreasing disease severity. Five to seven days following the last administration of neutralizing antibodies, disease severity returned to the level exhibited by control AA rats (not shown). This further emphasizes the advantageous of naked DNA vaccination over neutralizing antibody therapy.
Treatment of an Established Disease by MCP-1 Encoding DNA Vaccine:

The MCP-1naked DNA vaccine, administered before induction of disease was round to be highly effective in inhibiting the development and progression of AA, as determined by clinical scoring, measurements of limb swelling (FIGS. 1a–d), and histological analysis (FIGS. 2a–n). Thus the above DNA vaccine was selected as a preferred candidate for therapeutic experiments in which the vaccine is administered following disease establishment (FIGS. 8a–c).

Lewis rats were immunized with CFA to induce active AA and separated into three random groups of twelve rats each. Two of these groups were then subjected to three repeated administrations (days 10, 12, 14) of either pcDNA3 alone or of the MCP-1 construct (300 μg per rat). The third group was inoculated with PBS. While all control and pcDNA3 treated rats continued to develop severe AA, those administered with the MCP-1 DNA vaccine exhibited a substantially reduced form of the disease. As shown in FIGS. 8a–c, at day 25, a mean maximal score of 11±1 and 11.2±0.9 was determined for rats treated with either PBS or pcDNA3 alone as compared to a mean maximal score of 6.2±0.76, p<0.001for the MCP-1DNA vaccinated rats). The clinical score was confirmed by a histological analysis of synovitis, cartilage loss and bone erosion of representative joint sections obtained from all experimental groups (FIGS. 9a–p). Sections obtained from AA rats treated with the MCP-1 DNA construct displayed a marked reduction in each of the above parameters as compared to control and pcDNA3 treated AA rats (FIGS. 9a–p). The beneficial effect of the treatment was long lasting and covered not only the acute phase, but also the chronic phase of disease. Thus, 60 and 90 days following induction of the disease, AA rats treated with the MCP-1 DNA construct manifested a significantly reduced disease state as determined by both clinical scoring and histological analysis of the joints obtained during the acute (day 30) and chronic (day 90) phase of disease. During the acute phase of disease sections form PBS and pcDNA3 treated control rats displayed a massive inflammatory mononuclear cell infiltrate in the synovial membrane, an apparent increase in thickness of the synovial lining, narrowing of the joint space and notable periosteal new bone formation (FIGS. 9e–f and i–j). During the chronic phase of disease the intensity of the synovial leukocyte infiltration regressed, yet cartilage loss, bone erosion and periosteal new bone formation profoundly increased (FIGS. 9g–h and k–l). During the acute phase of disease sections form MCP-1 naked DNA treated rats displayed a substantial reduction in synovial leukocyte infiltration, synovitis, cartilage loss and bone erosion (FIGS. 9m–n) that resembled the histological analysis of sections from rats that were vaccinated with the MCP-1 DNA vaccine before the induction of active disease (FIGS. 2a–n). Interestingly, and most importantly, during the chronic phase of disease (day 90) massive cartilage loss, bone erosion and periosteal new bone formation that characterized control and pcDNA3 treated rats was entirely absent in joint sections of rats treated with MCP-1 naked DNA vaccine following induction of AA (FIGS. 9g–h, k–l and o–p).

Thus, naked DNA vaccination using a chemokine expressing construct especially an MCP-1 construct could serve as a highly effective method of treating ongoing arthritis in humans.

EXAMPLE 2

Results of Experiments Conducted with TNF-α
Prevention of AA using TNF-α Naked DNA Vaccine:

The cloned PCR product of TNF-α was ligated into a pcDNA3 mammalian expression vector and used as constructs for naked DNA vaccination. Lewis rats were exposed to four weekly administrations of this construct. Control rats were injected with either the β-actin construct, the pcDNA3 vector alone, or with PBS. Three weeks following the last immunization all rats were immunized with CFA to induce AA. Under working conditions established by the present study, AA manifests a long lasting form of disease that includes an acute phase, peaking around day 20, and a chronic phase that persists for more than 100 days (FIGS. 10a–d). All of the control rats which were treated with either PBS, pcDNA3 alone or β-actin pcDNA3 (12 per group) developed a severe form of disease with a maximal clinical score (day 20) of 13.5±1.8, 13±1.52 and 13±1.52 respectively (FIGS. 10a–d). In sharp contrast, rats subjected to the subsequent administration of TNF-α construct developed a significantly reduced form of the disease (mean maximal score of 6.7±1.1, p<0.001). A significantly reduced form of the disease was also recorded in these animals during the chronic phase of disease (day 45, 1.7±0.7 as compared to 7.2±0.77, 6.5±1 6.7±1.2 in the controls, p<0.001; day 90, 1±0.7 as compared to 3.3±0.8, 3.3±0.86 and 3.5±0.7, in the controls, p<0.001). In addition to clinical scoring, changes in paw swelling were recorded by an observer blind to the experimental procedure. At all times (days 20, 45 and 90) TNF-α DNA vaccinated rats exhibited a marked reduction in D paw swelling compared to each of the control groups (p<0.001, FIGS. 10a–d). Representative joint sections from all experimental groups (4 animals per group) were obtained on day 30) and screened for histological inflammatory mononuclear cell infiltrate in the synovial membrane, thickness of the synovial lining, joint space narrowing and periosteal new bone formation. Sections obtained from TNF-α DNA vaccinated rats displayed a marked reduction in each of the above parameters as compared to control and pcDNA3 treated AA rats (mean histological score of 12 sections from four animals, 0.5±0.2 in TNF-α DNA vaccinated rats compared to 2.8±0.2, 2.66±0.4 and 3±0 in pcDNA3, β-actin or PBS treated rats p<0.001 respectively). Thus, a TNF-α expressing naked DNA vaccination, could serve as a powerful tool for preventing AA.
Self-specific Antibodies Generated by DNA Vaccinated Rats Display in-vitro Neutralizing Capabilities, and in Addition are Capable of Transferring the Protective Effect of each Vaccine:

DNA vaccination can potentially elicit both cellular and humoral responses against products of a given construct (Donnelly et al., 1997; Fu et al., 1997; Tang et al., 1992;

Ulmer et al., 1993; Ulmer et al., 1996). To assess the contribution of the humoral response to the tolerant state, DNA vaccinated AA rats were followed during the generation of self-specific antibodies to TNF-α. The antibodies were evaluated for their ability to neutralize TNF-α (in-vitro) and to interfere in the development of AA in an adoptive transfer experiment.

Thus, Lewis rats were subjected to administration of PBS, pcDNA3 alone, the β-actin construct or a TNF-α naked DNA construct. Three weeks following administration these rats were separated to sub-groups that were immunized with CFA by either a foot pad injection to induce a local DTH response or a tail-base administration to induce poly-arthritis. The presence of anti-self antibody in the serum was determined at around the peak of the acute phase of the disease. Rats which developed poly-arthritis manifested a notable self-specific antibody titer to TNF-α (FIGS. 11a–b), but not to β-actin (data not shown), even in the absents of DNA vaccination. Interestingly, this titer differed in non-diseased rats, and in rats immunized to manifest a local DTH response (FIGS. 11a–c, day 20—$log_2Ab$ titer of 13±0.55 in AA rats as compared to 9±0.33 and 8±0.47 in rats with a local DTH response and non-diseased rats, respectively, $p<0.05$).

This notable increase in self-specific titer was not enough to prevent the development and progression of the inflammatory condition characterizing AA (FIGS. 10a–d). However, in TNF-α naked DNA vaccinated rats, TNF-α specific antibody titer increased following AA induction, and to a much lesser extent following the injection of CFA to induce a DTH response, (FIG. 11a—log2Ab titer of 25±1.2 Vs 16±0.8, $p<0.001$). The antibody titer continued to persist during the chronic phase of disease (FIG. 11c), as did the clinical effect of these vaccines (FIGS. 10a–d).

Antibodies were purified (IgG fraction, protein G purification) and evaluated for their competence to neutralize the activity of TNF-α (in-vitro) and transfer AA resistance. As shown by FIG. 12 Natural red uptake which serves to determine demonstrated that an IgG fraction from TNF-α DNA vaccinated rats is capable of abolishing the cytotoxic activity of TNF-α on U937 cytotoxic T cells. Thus antibodies produced in naked DNA vaccinated rats are neutralizing antibodies. These antibodies were then evaluated for ability to provide protection from severe ongoing AA (FIG. 13). Before being tested in-vivo (i.e. ability to affect the course of AA), sera obtained from all the experimental groups were purified (IgG purification). Sera from rats vaccinated with the TNF-α construct were also subjected to a purification on an activated TNF-α-CNBr Sepharose Column, as described hereinabove. Beginning on day 16 AA rats were challenged (i.v) with 100 μg of each of these antibodies. Control rats were injected with either PBS, IgG from non-diseased rats, IgG from AA or from AA rats previously administered with pcDNA3 alone. Repeated administration of TNF-α specific antibodies from DNA vaccinated rats led to a marked reduction in disease severity as compared to all control groups (day 20 mean maximal score of 2.25±0.7 compared to 9.5±1.6, 10±1.4, 10±0.7 and 10.5±1.4 in control AA rats treated with either PBS, IgG from AA rats, IgG from pcDNA3 vaccinated rats, or IgG from non-diseased rats $p<0.001$ for the comparison to each of the control groups). Clinical scoring was also determined by measuring limb swelling and histology (not shown).

The results obtained by this study may explain, in part, the effect of TNF-α DNA vaccination on disease manifestation. Five to seven days following the last administration of neutralizing antibodies, disease severity returned to the level exhibited by control AA rats (not shown). This further emphasizes the advantageous of naked DNA vaccination over neutralizing antibody therapy.

Treatment of an Established Disease by TNF-α Encoding DNA Vaccine:

The ability of the TNF-α naked DNA in interfering in the development and progression of an ongoing disease was tested in subjects in which the vaccine was administered only following the onset of disease.

Lewis rats were immunized with CFA to induce active AA and separated into tour random groups of twelve rats each. One day following the onset of disease (day 11) and on days 13 and 15 three of these groups were subjected to repeated administrations of either PBS, pcDNA3 alone, the β-actin construct or the TNF-α construct (300 μg per rat).

The control and pcDNA3 treated rats continued to develop severe AA, while those treated with the TNF-α DNA vaccine exhibited a markedly reduced form of the disease (FIG. 14). The marked reduction in the severity of the disease continued persisted throughout the chronic phase of the disease. Clinical scores were confirmed histologically (FIGS. 15a–p) on representative joint sections which were obtained on day 30 and 60 from all experimental groups and evaluated for histological analysis of synovitis, cartilage loss and bone erosion. Sections obtained from AA rats treated with the TNF-α DNA construct displayed a marked reduction in each of the above parameters as compared to control and pcDNA3 treated AA rats. The beneficial effect of the treatment was long lasting and covered the acute phase (day 30), and the chronic phase of the disease (day 60). During the acute phase of the disease sections from PBS and pcDNA3 treated control rats displayed a massive inflammatory mononuclear cell infiltrate in the synovial membrane, an apparent increase in thickness of the synovial lining, narrowing of the joint space and notable periosteal new bone formation (FIGS. 15e–f and i–j) while sections from TNF-α naked DNA treated rats displayed a substantial reduction in synovial leukocyte infiltration, synovitis, cartilage loss and bone erosion (FIGS. 15m–n). Interestingly, and most importantly, during the chronic phase of disease (day 60) massive cartilage loss, bone erosion and periosteal new bone formation which characterized control and pcDNA3 treated rats (FIGS. 15g–h and k–l) was entirely absent from joint sections of rats treated with TNF-α naked DNA vaccine following the induction of AA (FIGS. 15g–h).

Thus, naked DNA vaccination using a TNF-α expressing construct could be highly effective in treating ongoing arthritis in humans.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications cited herein are incorporated by reference in their entirety. Citation or identification of any reference in this application shall not be construed as an admission that such reference is available as prior art to the present invention.

REFERENCES

1. Arend, W. P., and Dayer, J. M. (1995). Inhibition of the production and effects of interleukin-1 and tumor necrosis factor alpha in rheumatoid arthritis. Arthritis Rheum 38, 151–60.
2. Arend, W. P., Malyak. M., Smith, M. F., Jr., Whisenand, T. D., Slack, J. L., Sims, J. E., Giri, J. G., and Dower, S.

K. (1994). Binding of IL-1 alpha, IL-1 beta, and IL-1 receptor antagonist by soluble IL-1 receptors and levels of soluble IL-1 receptors in synovial fluids. J Immunol 153, 4766–74.
3. Bacha, P., Forte. S. E., Perper, S. J., Trentham, D. E., and Nichols, J. C. (1992). Anti-arthritic effects demonstrated by an interleukin-2 receptor-targeted cytotoxin (DAB486IL-2) in rat adjuvant arthritis. Eur J Immunol 22, 1673–9.
4. Badolato, R., and Oppenheim, J. J. (1996). Role of cytokines, acute-phase proteins, and chemokines in the progression of rheumatoid arthritis. Semin Arthritis Rheum 26, 526–38.
5. Badolato, R., Ponzi, A. N., Millesimo, M., Notarangelo, L. D., and Musso, T. (1997). Interleukin-15 (IL-15) induces IL-8 and monocyte chemotactic protein 1 production in human monocytes. Blood 90, 2804–9.
6. Barnes, D. A., Tse, J., Kaufhold, M., Owen, M., Hesselgesser, J., Strieter, R., Horuk, R., and Perez, H. D. (1998). Polyclonal antibody directed against human RANTES ameliorates disease in the Lewis rat adjuvant-induced arthritis model. J Clin Invest 101, 2910–9.
7. Butler, D. M., Malfait, A. M., Maini, R. N., Brennan, F. M., and Feldmann, M. (1999). Anti-IL-12 and anti-TNF antibodies synergistically suppress the progression of murine collagen-induced arthritis. European Journal of Immunology 29, 2205–12.
8. Cash, E., Minty, A., Ferrara, P., Caput, D., Fradelizi, D., and Rott, O. (1994). Macrophage-inactivating IL-13 suppresses experimental autoimmune encephalomyelitis in rats. J Immunol 153, 4258–67.
9. Chabaud, M., Fossiez, F., Taupin, J. I., and Miossec, P. (1998). Enhancin effect of IL-17 on IL-1-induced IL-6 and leukemia inhibitory factor production by rheumatoid arthritis synoviocytes and its regulation by Th2 cytokines. Journal of Immunology 161, 409–14.
10. Chen, Y., Kuchroo, V. K., Inobe, J., Hafler, D., and Weiner, H. L. (1994). Regulatory T-cell clones induced by oral tolerance: Suppression of autoimmune encephalomyelitis. Science 265, 1237–1240.
11. Cyster, J. G., Hartley, S. B., and Goodnow, C. C. (1994). Competition for follicular niches excludes self-reactive cells from the recirculating B-cell repertoire [see comments]. Nature 371, 389–95.
12. Donnelly, J. J., Ulmer, J. B., and Liu, M. A. (1997). DNA vaccines. Life Sci 60, 163–72.
13. Elliott, M. J., Maini, R. N., Feldmann, M., Kalden, J. R., Antoni, C., Smolen, J. S., Leeb, B., Breedveld, F. C., Macfarlane, J. D., Bijl, H., and et al. (1994). Randomised double-blind comparison of chimeric monoclonal antibody to tumour necrosis factor alpha (cA2) versus placebo in rheumatoid arthritis. Lancet 344, 1105–10.
14. Evans, C. H., Ghivizzani, S. C., and Robbins, P. D. (1998). Blocking cytokines with genes. Journal of Leukocyte Biology 64, 55–61.
15. Feldmann, M., Brennan, F. M., and Maini, N. (1996). Role of cytokines in rheumatoid arthritis. Ann. Rev. Immumol 14, 397–440.
16. Feldmann, M., Elliot, M. J., Woody, J. N., and Maini, R. N. (1997). Anti-tumor necrosis factor-alpha therapy of rheumatoid arthritis. Adv Immunol 64, 283–350.
17. Friedman, A., and Weiner, H. L. (1994). Induction of anergy or active suppression following oral tolerance is determined by antigen dosage. Proc Natl Acad Sci U S A 91, 6688–6692.
18. Fu, T. M., Ulmer, J. B., Caulfield, M. J., Deck, R. R., Friedman, A., Wang, S., Liu, X., Donnelly, J. J., and Liu, M. A. (1997). Priming of cytotoxic T lymphocytes by DNA vaccines: requirement for professional antigen presenting cells and evidence for antigen transfer from myocytes. Mol Med 3, 362–71.
19. Gong, J. H., Ratkay, L. G., Waterfield, J. D., and Clark-Lewis, I. (1997). An antagonist of monocyte chemoattractant protein 1(MCP-1) inhibits arthritis in the MRL-1pr mouse model. J Exp Med 186, 131–7.
20. Green, L. L., Hardy, M. C., Maynard-Currie, C. E., Tsuda, H., Louie, D. M., Mendez, M. J., Abderrahim, H., Noguchi, M., Smith, D. H., Zeng, Y., and et al. (1994). Antigen-specific human monoclonal antibodies from mice engineered with human Ig heavy and light chain YACs. Nat Genet 7, 13–21.
21. Halloran, M. M., Woods, J. M., Strieter, R. M., Szekanecz, Z., Volin, M. V., Hosaka, S., Haines. G. K., 3rd, Kunkel, S. L., Burdick, M. D., Walz, A., and Koch, A. E. (1999). The role of an epithelial neutrophil-activating peptide-78-like protein in rat adjuvant-induced arthritis. Journal of Immunology 162, 7492–500.
22. Harris, E. D., Jr. (1990). Rheumatoid arthritis. Pathophysiology and implications for therapy [published erratum appears in N Engl J Med Oct. 4, 1990;323(14);996] [see comments]. New England Journal of Medicine 322, 1277–89.
23. Holoshitz, J., Naparstek, Y., Ben-Nun, A., and Cohen, I. R. (1983). Lines of T lymphocytes induce or vaccinate against autoimmune arthritis. Science 219, 56–8.
24. Janeway, C. A., Jr. (1992). The immune system evolved to discriminate infectious nonself from noninfectious self. Immunol Today 13, 11–6.
25. Karpus, W. J., Lukacs, N. W., McRae, B. L., Strieter, R. M., Kunkel, S. L., and Miller, S. D. (1995). An important role for the chemokine macrophage inflammatory protein-1 alpha in the pathogenesis of the T cell-mediated autoimmune disease, experimental autoimmune encephalomyelitis. J Immunol 155, 5003–10.
26. Kasama, T., Yamazaki, J., Hanaoka, R., Miwa, Y., Hatano, Y., Kobayashi, K., Negishi, M., Ide, H., and Adachi, M. (1999). Biphasic regulation of the development of murine type II collagen-induced arthritis by interleukin-12: possible involvement of endogenous interleukin-10 and tumor necrosis factor alpha. Arthritis & Rheumatism 42, 100–9.
27. Khoury, S. J., Hancock, W. W., and Weiner, H. L. (1992). Oral tolerance to myelin basic protein and natural recovery from experimental autoimmune encephalomyelitis are associated with downregulation of inflammatory cytokines and differential upregulation of transforming growth factor beta, interleukin 4, and prostaglandin E expression in the brain. J Exp Med 176, 1355–64.
28. Kuruvilla, A. P., Shah, R., Hochwald, G. M., Liggitt, H. D., Palladino, M. A., and Thorbecke, G. J. (1991). Protective effect of transforming growth factor beta 1 on experimental autoimmune diseases in mice. Proc Natl Acad Sci U S A 88, 2918–21.
29. Liblau, R. S., Singer. S. M., and McDevitt, H. O. (1994). Th1 and Th2 CD4+T-Cells in the pathogenesis of organ-specific autoimmune diseases. Immunol. Today in press.
30. Lider, O., Karin, N., Shinitzky, M., and Cohen, I. R. (1987). Therapeutic vaccination against adjuvant arthritis using autoimmune T-cells treated with hydrostatic pressure. Proc. Natl. Acad. Sci. U.S.A 84, 4577–4580.
31. Luo, Y., Ianing, J., Devi, S., Mak, J., Schall, T. J., and Dorf, M. E. (1994). Biologic activities of the murine beta-chemokine TCA3. J Immunol 153, 4616–24.
32. Ma, Y., Thornton, S., Duwel, L. E., Boivin, G. P., Giannini, E. H., Leiden, J. M., Bluestone, J. A., and Hirsch, R. (1998). Inhibition of collagen-induced arthritis in mice by viral IL-10 gene transfer. Journal of immunology 161, 1516–24.
33. Matzinger, P. (1994). Tolerance, danger, and the extended family. Annu Rev Immunol 12, 991–1045.
34. Moreland, L. W., Heck, L. W., Jr., and Koopman, W. J. (1997). Biologic agents for treating rheumatoid arthritis. Concepts and progress. Arthritis Rheum 40, 397–409.

35. Moreland, L. W., Margolies, G., Heck, L. W., Jr., Saway, A., Blosch, C., Hanna, R., and Koopman, W. J. (1996). Recombinant soluble tumor necrosis factor receptor (p80) fusion protein: toxicity and dose finding trial in refractory rheumatoid arthritis. J Rheumatol 23, 1849–55.

36. Novick, D., Kim, S. H., Fantuzzi, G., Reznikov, L. L., Dinarello, C. A., and Rubinstein, M. (1999). Interleukin-18 binding protein: a novel modulator of the Th1 cytokine response. Immunity 10, 127–36.

37. Parks, E., Strieter, R. M., Lukacs, N. W., Gauldie, J., Hitt, M., Graham, F. L., and Kunkel, S. L. (1998). Transient gene transfer of IL-12 regulates chemokine expression and disease severity in experimental arthritis. Journal of Immunology 160, 4615–9.

38. Pette, M., Fujita, K., Kitze, B., Whitaker, J. N., Albert, E., Kappos, L., and Wekerle, H. (1990). Myelin basic protein-specific T lymphocyte lines from MS patients and healthy individuals. Neurology 40, 1770–6.

39. Racke, M. K., Bonomo, A., Scott, D. E., Cannella, B., Levine, A., Raine, C. S., Shevach, E. M., and Rocken, M. (1994). Cytokine-induced immune deviation as a therapy for inflammatory autoimmune disease. J Exp Med 180, 1961–6.

40. Racke, M. K., Dhib, J. S., Cannella, B., Albert, P. S., Raine, C. S., and McFarlin, D. E. (1991). Prevention and treatment of chronic relapsing experimental allergic encephalomyelitis by transforming growth factor-beta 1. J Immunol 146, 3012–7.

41. Racke, M. K., Dhib-Jalbut, S., Cannella, B., Albert, P. S., Raine, C. S., and McFarlin, D. E. (1991). Prevention and treatment of chronic relapsing experimental allergic encephalomyelitis by transforming growth factor-beta 1. J Immunol 146.3012–7.

42. Rapoport, M. J., Jaramillo, A., Zipris. D., Lazarus, A., Serreze, D. V., Leiter, E. H., Cyopick, P., Danska, J. S., and Delovitch, T. L. (1993). Interleukin-4 reverses T cell proliferative unresponsiveness and prevents the onset of diabetes in nonobese diabetic mice. J. Exp. Med. 178. 87–99.

43. Raz, E., Tighe. H., Sato, Y., Corr, M., Dudler, J. A., Roman, M., Swain, S. L., Spiegelberg, H. L., and Carson, D. A. (1996). Preferential induction of a Th1 immune response and inhibition of specific IgE antibody formation by plasmid DNA immunization. Proc Natl Acad Sci U S A 93, 5141–5.

44. Ridge, J. P., Di Rosa, F., and Matzinger, P. (1998). A conditioned dendritic cell can be a temporal bridge between a CD4+T-helper and a T-killer cell [see comments]. Nature 393, 474–8.

45. Rollins, B. J. (1997). Chemokines. Blood 90, 909–928.

46. Sallusto, F., Lanzavecchia, A., and Mackay, C. R. (1998). Chemokines and chemokine receptors in T-cell priming and Th1/Th2-mediated responses. Immunol Today 19, 568–74.

47. Saoudi, A., Kuhn, J., Huygen, K., de, K. Y., Velu, T., Goldman, M., Druet, P., and Bellon, B. (1993). TH2 activated cells prevent experimental autoimmune uveoretinitis, a TH1-dependent autoimmune disease. Eur J Immunol 23, 3096–103.

48. Sato, M., Miyazaki, T., Nagaya, T., Murata, Y., Ida, N., Maeda, K., and Seo, H. (1996). Antioxidants inhibit tumor necrosis factor-alpha mediated stimulation of interleukin-8, monocyte chemoattractant protein-1, and collagenase expression in cultured human synovial cells. Journal of Rheumatology 23, 432–8.

49. Sato, Y., Roman, M., Tighe, H., Lee, D., Corr, M., Nguyen, M., Silverman, G. J., Lotz, M., Carson. D. A., and Raz, E. (1996). Immunostimulatoey DNA sequinces necessery for effective intradermal gene immunization. Science 273, 352–357.

50. Schimnier, R. C., Schrier, D. J., Flory, C. M., Laemont, K. D., Tung, D., Metz, A. L., Friedl, H. P., Conroy, M. C., Warren, J. S., Beck, B., and Ward, P. A. (1998). Streptococcal cell wall-induced arthritis: requirements for IL-4, IL-10. IFN-gamma, and monocyte chemoattractant protein-1. Journal of Immunology 160, 1466–71.

51. Schrier, D. J., Shimmer, R. C., Flory, C. M., Tung, D. K., and Ward, P. A. (1998). Role of chemokines and cytokines in a reactivation model of arthritis in rats induced by injection with streptococcal cell walls. Journal of Leukocyte Biology 63, 359–63.

52. Segal, B. M., Dwyer, B. K., and Shevach, E. M. (1998). An interleukin (IL)-10/IL-12 immunoregulatory circuit controls susceptibility to autoimmune disease. J Exp Med 187, 537–46.

53. Song, X. Y., Gu, M., Jin, W. W., Klinman, D. M., and Wahl, S. M. (1998). Plasmid DNA encoding transforming growth factor-betal suppresses chronic disease in a streptococcal cell wall-induced arthritis model. J Clin Invest 101, 2615–21.

54. Steinman, L. (1995). Escape from "horror autotoxicus": pathogenesis and treatment of autoimmune disease. Cell 80, 7–10.

55. Tang, D. C., DeVit, M., and Johnston. S. A. (1992). Genetic immunization is a simple method for eliciting an immune response. Nature 356. 152–4.

56. Ulmer, J. B., Donnelly, J. J., Parker, S. E., Rhodes, G. H., Felgner, P. L., Dwarki, V. J., Gromkowski, S. H., Deck, R. R., DeWitt, C. M., Friedman, A., and et al. (1993). Heterologous protection against influenza by injection of DNA encoding a viral protein [see comments]. Science 259, 1745–9.

57. Ulmer, J. B., Sadoff, J. C., and Liu, M. A. (1996). DNA vaccines. Current opinion in immunology 8, 531–536.

58. Wahl, S. M., Allen, J. B., Costa, G. L., Wong, H. L., and Dasch, J. R. (1993). Reversal of acute and chronic synovial inflammation by anti-transforming growth factor beta. J Exp Med 177, 225–30.

59. Ward, S. G., Bacon, K., and Westwick, J. (1998). Chemokines and T lymphocytes: more than an attraction. Immunity 9, 1–11.

60. Wildbaum, G., and Karin, N. (1999). Augmentation of natural immunity to a pro-inflammatory cytokine (TNF-a) by targeted DNA vaccine confers long lasting resistance to experimental autoimmune encephalomyelitis. Gene Therapy 6, 1128–1138.

61. Youssef, S., Wildbaum, G., and Karin, N. (1999). Prevention of Experimental Autoimmune Encephalomyelitis by MIP-1alpha and MCP-1 Naked DNA Vaccines. J Autoimmun 13, 21–29.

62. Youssef, S., Wildbaum, G., Maor, G., Lanir, N., Gour-Lavie, A., Grabie. N., and Karin, N. (1998). Long lasting protective immunity to experimental autoimmune encephalomyelitis following vaccination with naked DNA encoding C—C chemokines. J. Immunol 161, 3870–3879.

63. Yu, W., Nagaoca, H., Jankovic, M., Misulovin, Z., Suh, H., Rolink, A., Melchers, F., Meffre, E., and Nussenzweig, M. C. (1999). Continued RAG expression in late stages of B cell development and no apparent re-induction after immunization [see comments]. Nature 400. 682–7.

What is claimed is:

1. A method of treating rheumatoid arthritis of an individual, the method comprising intra-muscularly administering an exogenous polynucleotide encoding an immunogenic portion of a cytokine selected from the group of cytokines consisting of MIP-1α, MCP-1, MIP-1β, RANTES and TNF-α, operatively linked to a promoter, wherein the expression of said immunogenic portion induces a formation of antibodies to said immunogenic portion, wherein said antibodies reduce an in vivo activity of an endogenous cytokine of said cytokines, to thereby treat rheumatoid arthritis.

* * * * *

SEQUENCE LISTING

<160> NUMBER OF SEQ ID NOS: 12

<210> SEQ ID NO 1
<211> LENGTH: 26
<212> TYPE: DNA
<213> ORGANISM: synthetic oligonucleotide

<400> SEQUENCE: 1
atgaaggtct ccaccactgc ccttgc                                              26

<210> SEQ ID NO 2
<211> LENGTH: 25
<212> TYPE: DNA
<213> ORGANISM: synthetic oligonucleotide

<400> SEQUENCE: 2
tcaggcattc agttccagct cagtg                                               25

<210> SEQ ID NO 3
<211> LENGTH: 24
<212> TYPE: DNA
<213> ORGANISM: synthetic oligonucleotide

<400> SEQUENCE: 3
atgaagctct gcgtgtctgc cttc                                                24

<210> SEQ ID NO 4
<211> LENGTH: 24
<212> TYPE: DNA
<213> ORGANISM: synthetic oligonucleotide

<400> SEQUENCE: 4
tcagttcaac tccaagtcat tcac                                                24

<210> SEQ ID NO 5
<211> LENGTH: 24
<212> TYPE: DNA
<213> ORGANISM: synthetic oligonucleotide

<400> SEQUENCE: 5
atgaagatct ctgcagctgc atcc                                                24

<210> SEQ ID NO 6
<211> LENGTH: 22
<212> TYPE: DNA
<213> ORGANISM: synthetic oligonucleotide

<400> SEQUENCE: 6
ctagctcatc tccaaatagt tg                                                  22

<210> SEQ ID NO 7
<211> LENGTH: 27
<212> TYPE: DNA
<213> ORGANISM: synthetic oligonucleotide

<400> SEQUENCE: 7
atgcaggtct ctgtcacgct tctgggc                                             27

<210> SEQ ID NO 8
<211> LENGTH: 24
<212> TYPE: DNA
<213> ORGANISM: synthetic oligonucleotide

```
<400> SEQUENCE: 8
ctagttctct gtcatactgg tcac                                          24

<210> SEQ ID NO 9
<211> LENGTH: 20
<212> TYPE: DNA
<213> ORGANISM: synthetic oligonucleotide

<400> SEQUENCE: 9
atgagcacag aaagcatgat                                               20

<210> SEQ ID NO 10
<211> LENGTH: 21
<212> TYPE: DNA
<213> ORGANISM: synthetic oligonucleotide

<400> SEQUENCE: 10
tcacagagca atgactccaa a                                             21

<210> SEQ ID NO 11
<211> LENGTH: 24
<212> TYPE: DNA
<213> ORGANISM: synthetic oligonucleotide

<400> SEQUENCE: 11
atggatgacg atatcgctgc gctc                                          24

<210> SEQ ID NO 12
<211> LENGTH: 18
<212> TYPE: DNA
<213> ORGANISM: synthetic oligonucleotide

<400> SEQUENCE: 12
ctaccggcca gccagacg                                                 18
```